United States Patent [19]
Zhang et al.

[11] Patent Number: 6,137,031
[45] Date of Patent: Oct. 24, 2000

[54] DNA BINDING PROTEINS THAT INTERACT WITH NPR1

[75] Inventors: Yuelin Zhang, Davis, Calif.; Mark Kinkema; Xinnian Dong, both of Durham, N.C.; Pamela Ronald; Maw Shenq Chern, both of Davis, Calif.

[73] Assignees: Duke University, Durham, N.C.; The Regents of the University of California, Oakland, Calif.

[21] Appl. No.: 09/267,031

[22] Filed: Mar. 11, 1999

[51] Int. Cl.[7] ........................... C12N 15/29; C12N 15/63; C12N 15/82; A01H 5/00

[52] U.S. Cl. ..................... 800/279; 800/301; 800/287; 800/317.4; 800/320.2; 536/23.1; 536/23.6; 536/24.1; 435/468; 435/69.1

[58] Field of Search ................................. 800/279, 301, 800/287, 317.4, 320.2, 320.3, 317.3, 320.1; 536/23.1, 23.4, 23.6, 24.1; 435/252.3, 69.1, 468

[56] References Cited

U.S. PATENT DOCUMENTS

| | | | |
|---|---|---|---|
| 4,990,607 | 2/1991 | Katagiri et al. | 536/27 |
| 5,623,054 | 4/1997 | Zhang et al. | 530/370 |

OTHER PUBLICATIONS

Xiang, et al., "DNA–binding properties, genomic organization and expression pattern of TGA6, a new member of the TGA family of bZIP transcription factors in *Arabidopsis thaliana*"; *Plant Molecular Biology* 34: 403–415 (1997).

Kawata, et al., "A cDNA clone encoding HBP–1b homologue in *Arabidopsis thaliana*"; vol. 20, No. 5, p. 1141 (1992).

Zhang, et al., "Isolation and characterization of two related *Arabidopsis ocs*–element bZIP binding proteins"; *The Plant Journal* 4(4), pp. 711–716 (1993).

Jupin, et al., "Activation of the CaMV as–1 cis–element by salicylic acid: differential DNA–binding of a factor related to TGA1a"; *The EMBO Journal*, vol. 15, No. 20, pp. 5679–5689 (1996).

Lebel, et al., "Functional analysis of regulatory sequences controlling PR–1 gene expression in Arabidopsis"; *The Plant Journal*, 16(2), pp. 223–233 (1998).

Cao, et al., "The Arabidopsis NPR1 Gene That Controls Systemic Acquired Resistance Encodes a Novel Portein Containing Ankyrin Repeats"; *Cell*, vol. 88, pp. 57–63 (Jan. 10, 1977).

Baranger, "Accessory factor–bZIP–DNA interactions"; *Current Opinion in Chemical Biology*, 2:18–23 (1998).

Horvath, et al., "Four Classes of Salicylate–Induced Tobacco Genes"; *Molecular Plant–Microbe Interactions*, vol. 11, No. 9, pp. 895–905 (1998).

Stange, et al., "Phosphorylation of nuclear proteins directs binding to salicylic acid–responsive elements"; *The Plant Journal*, 11(6), pp. 1315–1324 (1997).

Lam, et al., "Binding site requirements and differential representation of TGA factors in nuclear ASF–1 activity"; *Nucleic Acids Research*, vol. 23, No. 18, pp. 3778–3785 (1995).

Miao, et al. "TGA3 is a distinct member of the TGA family of bZIP transcription factors in *Arabidopsis thaliana*"; *Plant Molecular Biology* 25: 1–11 (1994).

Schindler, et al., "TGA1 and G–Box Binding Factors: Two Distinct Classes of Arabidopsis Leucine Zipper Proteins Complete for the G–Box–Like Element TGACGTGG"; *The Plant Cell*, vol. 4, 1309–1319 (Oct. 1992).

Bennetzen et al. Genetic Engineering, vol. 14, 99–124, 1992.

Linthorst et al. The Plant Cell vol. 1, pp. 285–291, Mar. 1989.

Niggeweg et al. Plant Physiology vol. 113, 1464, 1997.

Walsh et al. Genes and Development 11:208–218, 1997.

CAO et al. Proc. Natl. Acad, Sci. USA vol. 95, pp. 6531–6536, 1998.

Tabata et al. The Embo Journal vol. No. 6, pp. 1459–1467, 1991.

*Primary Examiner*—David T. Fox
*Assistant Examiner*—Medina A. Ibrahim
*Attorney, Agent, or Firm*—Townsend and Townsend and Crew LLP

[57] ABSTRACT

The present invention provides nucleic acids that encode bZIP polypeptides that are capable of interacting with NPR1. The present invention also provides for bZIP polypeptides that are capable of interacting with NPR1 as well as transgenic plants comprising a nucleic acids that encode bZIP polypeptides that are capable of interacting with NPR1. Also provided by the present invention is a method for enhancing resistance of plants to pathogens by introducing a recombinant expression cassette comprising a plant promoter operably linked to a polynucleotide sequence encoding a bZIP polypeptide that interacts with NPR1. The present invention also provides for a method of identifying additional bZIP polypeptides that interact with NPR1.

46 Claims, No Drawings

SEQUENCE LISTING

<160> NUMBER OF SEQ ID NOS: 26

<210> SEQ ID NO 1
<211> LENGTH: 1005
<212> TYPE: DNA
<213> ORGANISM: Oryza sp.

-continued

```
<220> FEATURE:
<221> NAME/KEY: CDS
<222> LOCATION: (1)..(1005)
<223> OTHER INFORMATION: rice bZIP gene MN1

<400> SEQUENCE: 1
```

| | | | | | | | | | | | | | | | | |
|---|---|---|---|---|---|---|---|---|---|---|---|---|---|---|---|---|
| atg | gca | gat | gct | agt | tca | agg | act | gac | aca | tcg | att | gtt | gta | gac | aac | 48 |
| Met | Ala | Asp | Ala | Ser | Ser | Arg | Thr | Asp | Thr | Ser | Ile | Val | Val | Asp | Asn | |
| 1 | | | | 5 | | | | | 10 | | | | | 15 | | |
| gac | gac | aaa | aac | cac | cag | tta | gaa | aac | gga | cat | agt | ggt | gca | gtc | atg | 96 |
| Asp | Asp | Lys | Asn | His | Gln | Leu | Glu | Asn | Gly | His | Ser | Gly | Ala | Val | Met | |
| | | | 20 | | | | | 25 | | | | | 30 | | | |
| gct | tct | aac | tct | tca | gat | aga | tct | gac | aga | tct | gac | aaa | ctt | atg | gac | 144 |
| Ala | Ser | Asn | Ser | Ser | Asp | Arg | Ser | Asp | Arg | Ser | Asp | Lys | Leu | Met | Asp | |
| | | 35 | | | | | 40 | | | | | 45 | | | | |
| caa | aag | aca | atg | cgg | cgg | ctt | gct | caa | aat | cgt | gag | gca | gca | aga | aaa | 192 |
| Gln | Lys | Thr | Met | Arg | Arg | Leu | Ala | Gln | Asn | Arg | Glu | Ala | Ala | Arg | Lys | |
| 50 | | | | | 55 | | | | | 60 | | | | | | |
| agt | cgg | ctg | agg | aaa | aag | gca | tat | gtg | caa | caa | cta | gag | agc | agt | aag | 240 |
| Ser | Arg | Leu | Arg | Lys | Lys | Ala | Tyr | Val | Gln | Gln | Leu | Glu | Ser | Ser | Lys | |
| 65 | | | | | 70 | | | | | 75 | | | | | 80 | |
| ctg | aag | ctt | gca | cag | cta | gag | cag | gaa | ctt | cag | aaa | gct | cgt | cag | cag | 288 |
| Leu | Lys | Leu | Ala | Gln | Leu | Glu | Gln | Glu | Leu | Gln | Lys | Ala | Arg | Gln | Gln | |
| | | | | 85 | | | | | 90 | | | | | 95 | | |
| gga | atc | ttc | atc | tct | agc | tct | gga | gac | cag | acc | cat | gcc | atg | agt | gga | 336 |
| Gly | Ile | Phe | Ile | Ser | Ser | Ser | Gly | Asp | Gln | Thr | His | Ala | Met | Ser | Gly | |
| | | | 100 | | | | | 105 | | | | | 110 | | | |
| aat | ggg | gca | ttg | act | ttt | gac | tta | gaa | tac | act | aga | tgg | ctc | gag | gag | 384 |
| Asn | Gly | Ala | Leu | Thr | Phe | Asp | Leu | Glu | Tyr | Thr | Arg | Trp | Leu | Glu | Glu | |
| | | 115 | | | | | 120 | | | | | 125 | | | | |
| caa | aat | aag | cag | ata | aat | gag | ttg | agg | aca | gca | gtg | aat | gct | cat | gca | 432 |
| Gln | Asn | Lys | Gln | Ile | Asn | Glu | Leu | Arg | Thr | Ala | Val | Asn | Ala | His | Ala | |
| 130 | | | | | 135 | | | | | 140 | | | | | | |
| agt | gac | agt | gac | ctt | cgt | ctt | att | gtt | gat | ggc | ata | atg | gcg | cat | tat | 480 |
| Ser | Asp | Ser | Asp | Leu | Arg | Leu | Ile | Val | Asp | Gly | Ile | Met | Ala | His | Tyr | |
| 145 | | | | | 150 | | | | | 155 | | | | | 160 | |
| gac | gag | gta | ttc | aag | gtt | aag | ggt | gta | gct | gca | aag | gcc | gat | gtg | ttt | 528 |
| Asp | Glu | Val | Phe | Lys | Val | Lys | Gly | Val | Ala | Ala | Lys | Ala | Asp | Val | Phe | |
| | | | | 165 | | | | | 170 | | | | | 175 | | |
| cat | ata | ctt | tca | ggc | atg | tgg | aag | aca | ccc | gca | gaa | aga | tgc | ttc | ctg | 576 |
| His | Ile | Leu | Ser | Gly | Met | Trp | Lys | Thr | Pro | Ala | Glu | Arg | Cys | Phe | Leu | |
| | | | 180 | | | | | 185 | | | | | 190 | | | |
| tgg | ctt | ggt | ggt | ttc | cgt | cca | tct | gag | ctt | cta | aag | ctc | cta | gca | aat | 624 |
| Trp | Leu | Gly | Gly | Phe | Arg | Pro | Ser | Glu | Leu | Leu | Lys | Leu | Leu | Ala | Asn | |
| | | 195 | | | | | 200 | | | | | 205 | | | | |
| cac | ctc | gaa | cct | tta | acc | gag | cag | cag | ttg | ctg | gga | tta | aac | aac | ctc | 672 |
| His | Leu | Glu | Pro | Leu | Thr | Glu | Gln | Gln | Leu | Leu | Gly | Leu | Asn | Asn | Leu | |
| 210 | | | | | 215 | | | | | 220 | | | | | | |
| cag | gaa | tct | tct | cag | cag | gcg | gag | gat | gca | ctt | tca | caa | ggt | atg | gaa | 720 |
| Gln | Glu | Ser | Ser | Gln | Gln | Ala | Glu | Asp | Ala | Leu | Ser | Gln | Gly | Met | Glu | |
| 225 | | | | | 230 | | | | | 235 | | | | | 240 | |
| gca | ctg | cag | caa | tct | ctg | gca | gat | act | ttg | gct | gga | tct | ctc | gct | tca | 768 |
| Ala | Leu | Gln | Gln | Ser | Leu | Ala | Asp | Thr | Leu | Ala | Gly | Ser | Leu | Ala | Ser | |
| | | | | 245 | | | | | 250 | | | | | 255 | | |
| tca | ggg | tct | tct | ggg | aat | gtg | gcg | aac | tac | atg | ggt | cag | atg | gca | atg | 816 |
| Ser | Gly | Ser | Ser | Gly | Asn | Val | Ala | Asn | Tyr | Met | Gly | Gln | Met | Ala | Met | |
| | | | 260 | | | | | 265 | | | | | 270 | | | |
| gcc | atg | ggt | aaa | cta | gga | acg | ctc | gag | aat | ttc | ctt | tgc | cag | gcg | gac | 864 |
| Ala | Met | Gly | Lys | Leu | Gly | Thr | Leu | Glu | Asn | Phe | Leu | Cys | Gln | Ala | Asp | |
| | | 275 | | | | | 280 | | | | | 285 | | | | |

```
aac ctg cga cag cag aca ttg cat caa atg caa cga att ctg acg atc     912
Asn Leu Arg Gln Gln Thr Leu His Gln Met Gln Arg Ile Leu Thr Ile
    290                 295                 300 cgg caa gcc tcg cgt gct ctt ctt gcc ata cac gat tac ttt tca cgc     960
Arg Gln Ala Ser Arg Ala Leu Leu Ala Ile His Asp Tyr Phe Ser Arg
305                 310                 315                 320 ttg cgt gct ttg agt tcg ctg tgg ctt gct agg cca cgg gag taa        1005
Leu Arg Ala Leu Ser Ser Leu Trp Leu Ala Arg Pro Arg Glu
                325                 330
```

<210> SEQ ID NO 2
<211> LENGTH: 334
<212> TYPE: PRT
<213> ORGANISM: Oryza sp.

<400> SEQUENCE: 2

```
Met Ala Asp Ala Ser Ser Arg Thr Asp Thr Ser Ile Val Val Asp Asn
 1               5                  10                  15

Asp Asp Lys Asn His Gln Leu Glu Asn Gly His Ser Gly Ala Val Met
            20                  25                  30

Ala Ser Asn Ser Ser Asp Arg Ser Asp Arg Ser Asp Lys Leu Met Asp
         35                  40                  45

Gln Lys Thr Met Arg Arg Leu Ala Gln Asn Arg Glu Ala Ala Arg Lys
     50                  55                  60

Ser Arg Leu Arg Lys Lys Ala Tyr Val Gln Gln Leu Glu Ser Ser Lys
 65                  70                  75                  80

Leu Lys Leu Ala Gln Leu Glu Gln Glu Leu Gln Lys Ala Arg Gln Gln
                 85                  90                  95

Gly Ile Phe Ile Ser Ser Ser Gly Asp Gln Thr His Ala Met Ser Gly
            100                 105                 110

Asn Gly Ala Leu Thr Phe Asp Leu Glu Tyr Thr Arg Trp Leu Glu Glu
        115                 120                 125

Gln Asn Lys Gln Ile Asn Glu Leu Arg Thr Ala Val Asn Ala His Ala
    130                 135                 140

Ser Asp Ser Asp Leu Arg Leu Ile Val Asp Gly Ile Met Ala His Tyr
145                 150                 155                 160

Asp Glu Val Phe Lys Val Lys Gly Val Ala Ala Lys Ala Asp Val Phe
                165                 170                 175

His Ile Leu Ser Gly Met Trp Lys Thr Pro Ala Glu Arg Cys Phe Leu
            180                 185                 190

Trp Leu Gly Gly Phe Arg Pro Ser Glu Leu Leu Lys Leu Leu Ala Asn
        195                 200                 205

His Leu Glu Pro Leu Thr Glu Gln Gln Leu Leu Gly Leu Asn Asn Leu
    210                 215                 220

Gln Glu Ser Ser Gln Gln Ala Glu Asp Ala Leu Ser Gln Gly Met Glu
225                 230                 235                 240

Ala Leu Gln Gln Ser Leu Ala Asp Thr Leu Ala Gly Ser Leu Ala Ser
                245                 250                 255

Ser Gly Ser Gly Asn Val Ala Asn Tyr Met Gly Gln Met Ala Met
            260                 265                 270

Ala Met Gly Lys Leu Gly Thr Leu Glu Asn Phe Leu Cys Gln Ala Asp
        275                 280                 285

Asn Leu Arg Gln Gln Thr Leu His Gln Met Gln Arg Ile Leu Thr Ile
    290                 295                 300

Arg Gln Ala Ser Arg Ala Leu Leu Ala Ile His Asp Tyr Phe Ser Arg
305                 310                 315                 320
```

```
Leu Arg Ala Leu Ser Ser Leu Trp Leu Ala Arg Pro Arg Glu
                325                 330

<210> SEQ ID NO 3
<211> LENGTH: 1002
<212> TYPE: DNA
<213> ORGANISM: Oryzias sp.
<220> FEATURE:
<221> NAME/KEY: CDS
<222> LOCATION: (1)..(1002)
<223> OTHER INFORMATION: rice bZIP gene MN8

<400> SEQUENCE: 3 atg gca gat gct agt tcg agg act gac aca tca aca gtc ctg gat acc       48
Met Ala Asp Ala Ser Ser Arg Thr Asp Thr Ser Thr Val Leu Asp Thr
 1               5                  10                  15 gac gat aag aat cag atg gta gac ggg caa agt gga gct att gtg cct       96
Asp Asp Lys Asn Gln Met Val Asp Gly Gln Ser Gly Ala Ile Val Pro
             20                  25                  30 tct aat tca tct gat cgg tct gac aga tct gac aag ccc atg gac caa      144
Ser Asn Ser Ser Asp Arg Ser Asp Arg Ser Asp Lys Pro Met Asp Gln
         35                  40                  45 aag gtg tta cgc cgg ctt gct caa aat cgt gag gct gca aga aaa agt      192
Lys Val Leu Arg Arg Leu Ala Gln Asn Arg Glu Ala Ala Arg Lys Ser
     50                  55                  60 cgg ctg aga aaa aag gca tat gta caa caa tta gag agc agt aag ctg      240
Arg Leu Arg Lys Lys Ala Tyr Val Gln Gln Leu Glu Ser Ser Lys Leu
 65                  70                  75                  80 aaa ctt gca agc ttg gag caa gag atc aat aaa gct cgc caa caa gga      288
Lys Leu Ala Ser Leu Glu Gln Glu Ile Asn Lys Ala Arg Gln Gln Gly
                 85                  90                  95 att tac att tcg agc tca gga gac caa act cat gct atg agt gga aat      336
Ile Tyr Ile Ser Ser Ser Gly Asp Gln Thr His Ala Met Ser Gly Asn
            100                 105                 110 gga gct atg act ttt gat tta gaa tat gcc cgt tgg ttg gag gaa caa      384
Gly Ala Met Thr Phe Asp Leu Glu Tyr Ala Arg Trp Leu Glu Glu Gln
        115                 120                 125 aac aag cag ata aat gag ctg agg act gca gta aat gct cat gca agt      432
Asn Lys Gln Ile Asn Glu Leu Arg Thr Ala Val Asn Ala His Ala Ser
    130                 135                 140 gac agc gac ctc cgt ctc att gta gat ggg ata atg gcg cat tac gat      480
Asp Ser Asp Leu Arg Leu Ile Val Asp Gly Ile Met Ala His Tyr Asp
145                 150                 155                 160 gag ata ttc agg ctg aag ggt gtt gcc gca aag gct gat gtg ttt cat      528
Glu Ile Phe Arg Leu Lys Gly Val Ala Ala Lys Ala Asp Val Phe His
                165                 170                 175 ata ctt tca ggc atg tgg aaa aca cct gct gaa agg tgc ttc ttg tgg      576
Ile Leu Ser Gly Met Trp Lys Thr Pro Ala Glu Arg Cys Phe Leu Trp
            180                 185                 190 ctt ggg ggt ttt cgt tcc tct gag ctt cta aag ctt ctt gtg aat cag      624
Leu Gly Gly Phe Arg Ser Ser Glu Leu Leu Lys Leu Leu Val Asn Gln
        195                 200                 205 ctc gag cca tta act gag cag cag ttg ttg gga cta tcg aac ctc caa      672
Leu Glu Pro Leu Thr Glu Gln Gln Leu Leu Gly Leu Ser Asn Leu Gln
    210                 215                 220 cag tcc tct cag cag gct gaa gat gct cta tca cag gga atg gaa gcg      720
Gln Ser Ser Gln Gln Ala Glu Asp Ala Leu Ser Gln Gly Met Glu Ala
225                 230                 235                 240 ttg caa caa tcc ttg gca gat acg ttg gcc ggg tcc ctt ggt cca tca      768
Leu Gln Gln Ser Leu Ala Asp Thr Leu Ala Gly Ser Leu Gly Pro Ser
                245                 250                 255
```

```
gga tct tca ggg aac gtg gca aac tac atg ggt caa atg gct atg gcc      816
Gly Ser Ser Gly Asn Val Ala Asn Tyr Met Gly Gln Met Ala Met Ala
            260                 265                 270 atg ggc aaa ctt ggg acc ctt gag aat ttc ctc cgt cag gct gac aat      864
Met Gly Lys Leu Gly Thr Leu Glu Asn Phe Leu Arg Gln Ala Asp Asn
        275                 280                 285 ttg cgg cag cag act tta cat caa atg cag cga att ctg aca atc cga      912
Leu Arg Gln Gln Thr Leu His Gln Met Gln Arg Ile Leu Thr Ile Arg
    290                 295                 300 caa gct gcc cgt gct cta ctt gca ata cat gat tac ttc tca cgt ttg      960
Gln Ala Ala Arg Ala Leu Leu Ala Ile His Asp Tyr Phe Ser Arg Leu
305                 310                 315                 320 cgt gcc ctg agt tct ctc tgg ctt gct agg cca cgg gag taa              1002
Arg Ala Leu Ser Ser Leu Trp Leu Ala Arg Pro Arg Glu
                325                 330

<210> SEQ ID NO 4
<211> LENGTH: 333
<212> TYPE: PRT
<213> ORGANISM: Oryzias sp.

<400> SEQUENCE: 4

Met Ala Asp Ala Ser Ser Arg Thr Asp Thr Ser Thr Val Leu Asp Thr
 1               5                  10                  15

Asp Asp Lys Asn Gln Met Val Asp Gly Gln Ser Gly Ala Ile Val Pro
             20                  25                  30

Ser Asn Ser Ser Asp Arg Ser Asp Arg Ser Asp Lys Pro Met Asp Gln
         35                  40                  45

Lys Val Leu Arg Arg Leu Ala Gln Asn Arg Glu Ala Ala Arg Lys Ser
     50                  55                  60

Arg Leu Arg Lys Lys Ala Tyr Val Gln Gln Leu Glu Ser Ser Lys Leu
 65                  70                  75                  80

Lys Leu Ala Ser Leu Glu Gln Glu Ile Asn Lys Ala Arg Gln Gln Gly
                 85                  90                  95

Ile Tyr Ile Ser Ser Ser Gly Asp Gln Thr His Ala Met Ser Gly Asn
            100                 105                 110

Gly Ala Met Thr Phe Asp Leu Glu Tyr Ala Arg Trp Leu Glu Glu Gln
        115                 120                 125

Asn Lys Gln Ile Asn Glu Leu Arg Thr Ala Val Asn Ala His Ala Ser
    130                 135                 140

Asp Ser Asp Leu Arg Leu Ile Val Asp Gly Ile Met Ala His Tyr Asp
145                 150                 155                 160

Glu Ile Phe Arg Leu Lys Gly Val Ala Ala Lys Ala Asp Val Phe His
                165                 170                 175

Ile Leu Ser Gly Met Trp Lys Thr Pro Ala Glu Arg Cys Phe Leu Trp
            180                 185                 190

Leu Gly Gly Phe Arg Ser Ser Glu Leu Leu Lys Leu Leu Val Asn Gln
        195                 200                 205

Leu Glu Pro Leu Thr Glu Gln Gln Leu Leu Gly Leu Ser Asn Leu Gln
    210                 215                 220

Gln Ser Ser Gln Gln Ala Glu Asp Ala Leu Ser Gln Gly Met Glu Ala
225                 230                 235                 240

Leu Gln Gln Ser Leu Ala Asp Thr Leu Ala Gly Ser Leu Gly Pro Ser
                245                 250                 255

Gly Ser Ser Gly Asn Val Ala Asn Tyr Met Gly Gln Met Ala Met Ala
            260                 265                 270
```

```
Met Gly Lys Leu Gly Thr Leu Glu Asn Phe Leu Arg Gln Ala Asp Asn
            275                 280                 285

Leu Arg Gln Gln Thr Leu His Gln Met Gln Arg Ile Leu Thr Ile Arg
        290                 295                 300

Gln Ala Ala Arg Ala Leu Leu Ala Ile His Asp Tyr Phe Ser Arg Leu
305                 310                 315                 320

Arg Ala Leu Ser Ser Leu Trp Leu Ala Arg Pro Arg Glu
                325                 330

<210> SEQ ID NO 5
<211> LENGTH: 925
<212> TYPE: DNA
<213> ORGANISM: Oryza sp.
<220> FEATURE:
<221> NAME/KEY: CDS
<222> LOCATION: (2)..(925)
<223> OTHER INFORMATION: rice bZIP gene MN38

<400> SEQUENCE: 5 a cca ggt cag ctt gct ctt gct gct gct tct gac tct gac aga tcc aag     49
  Pro Gly Gln Leu Ala Leu Ala Ala Ala Ser Asp Ser Asp Arg Ser Lys
    1               5                  10                  15 gac aaa cat gaa gat caa aag aca ttg cgt cgg ctc gcc caa aat cgc      97
Asp Lys His Glu Asp Gln Lys Thr Leu Arg Arg Leu Ala Gln Asn Arg
             20                  25                  30 gag gct gca agg aag agt cgt ttg agg aaa aag gca tat gtt caa caa     145
Glu Ala Ala Arg Lys Ser Arg Leu Arg Lys Lys Ala Tyr Val Gln Gln
         35                  40                  45 ttg gag aat agc agg cta aag ctt aca caa cta gaa caa gaa ttg caa     193
Leu Glu Asn Ser Arg Leu Lys Leu Thr Gln Leu Glu Gln Glu Leu Gln
     50                  55                  60 cga gct cgt cag cag ggc att ttt ata tcc agc tca gtg gac cag act     241
Arg Ala Arg Gln Gln Gly Ile Phe Ile Ser Ser Ser Val Asp Gln Thr
 65                  70                  75                  80 cat tcc atg agt gga aat ggg gca ttg gct ttt gat atg gag tat gca     289
His Ser Met Ser Gly Asn Gly Ala Leu Ala Phe Asp Met Glu Tyr Ala
                 85                  90                  95 cgt tgg ttg gaa gaa cac aat agg caa att aat gag cta agg tct gca     337
Arg Trp Leu Glu Glu His Asn Arg Gln Ile Asn Glu Leu Arg Ser Ala
            100                 105                 110 gtc aat gct cat gca ggt gat aat gag ctc cgt ggt gtt gtt gac aag     385
Val Asn Ala His Ala Gly Asp Asn Glu Leu Arg Gly Val Val Asp Lys
        115                 120                 125 atc atg tca cac tat gag gag att ttc aag cag aaa gga aat gcg gcc     433
Ile Met Ser His Tyr Glu Glu Ile Phe Lys Gln Lys Gly Asn Ala Ala
    130                 135                 140 aaa gca gat gtc ttt cat gtg tta tca ggc atg tgg aag aca cca gct     481
Lys Ala Asp Val Phe His Val Leu Ser Gly Met Trp Lys Thr Pro Ala
145                 150                 155                 160 gag agg tgt ttc ttg tgg cta gga gga ttc cga cca tcc gag ctt tta     529
Glu Arg Cys Phe Leu Trp Leu Gly Gly Phe Arg Pro Ser Glu Leu Leu
                165                 170                 175 aag ctt ctt tcg aca cag ctt gaa cct ctc act gag cag cag ctg tca     577
Lys Leu Leu Ser Thr Gln Leu Glu Pro Leu Thr Glu Gln Gln Leu Ser
            180                 185                 190 ggg ata gcc aac ctt cag cag tct tca caa caa gct gaa gat gct ctt     625
Gly Ile Ala Asn Leu Gln Gln Ser Ser Gln Gln Ala Glu Asp Ala Leu
        195                 200                 205 tca caa gga atg gag gcc ctt cag cag tcc ttg gca gaa aca ttg gct     673
Ser Gln Gly Met Glu Ala Leu Gln Gln Ser Leu Ala Glu Thr Leu Ala
    210                 215                 220
```

-continued

```
ggg tct ctt ggt tct tct gga tca acg gga aac gtg gca aac tac atg    721
Gly Ser Leu Gly Ser Ser Gly Ser Thr Gly Asn Val Ala Asn Tyr Met
225                 230                 235                 240 ggc caa atg gca atg gcc atg ggg aag ctt ggg acc ctt gag aat ttc    769
Gly Gln Met Ala Met Ala Met Gly Lys Leu Gly Thr Leu Glu Asn Phe
            245                 250                 255 ctt cgc cag gct gac aac ctg cgg cag cag act ctt caa cag atg caa    817
Leu Arg Gln Ala Asp Asn Leu Arg Gln Gln Thr Leu Gln Gln Met Gln
    260                 265                 270 agg ata ctg acc act agg cag tct gcc cgt gcg ctt ctt gtg ata agc    865
Arg Ile Leu Thr Thr Arg Gln Ser Ala Arg Ala Leu Leu Val Ile Ser
275                 280                 285 gat tac tct tcg cgg ctt cgt gcc ctt agt tcc ctc tgg ctt gct cgg    913
Asp Tyr Ser Ser Arg Leu Arg Ala Leu Ser Ser Leu Trp Leu Ala Arg
    290                 295                 300 ccg aaa gaa tag                                                    925
Pro Lys Glu
305

<210> SEQ ID NO 6
<211> LENGTH: 307
<212> TYPE: PRT
<213> ORGANISM: Oryza sp.

<400> SEQUENCE: 6

Pro Gly Gln Leu Ala Leu Ala Ala Ser Asp Ser Asp Arg Ser Lys
 1               5                  10                  15

Asp Lys His Glu Asp Gln Lys Thr Leu Arg Arg Leu Ala Gln Asn Arg
                20                  25                  30

Glu Ala Ala Arg Lys Ser Arg Leu Arg Lys Lys Ala Tyr Val Gln Gln
            35                  40                  45

Leu Glu Asn Ser Arg Leu Lys Leu Thr Gln Leu Glu Gln Glu Leu Gln
        50                  55                  60

Arg Ala Arg Gln Gln Gly Ile Phe Ile Ser Ser Val Asp Gln Thr
65                  70                  75                  80

His Ser Met Ser Gly Asn Gly Ala Leu Ala Phe Asp Met Glu Tyr Ala
                85                  90                  95

Arg Trp Leu Glu Glu His Asn Arg Gln Ile Asn Glu Leu Arg Ser Ala
            100                 105                 110

Val Asn Ala His Ala Gly Asp Asn Glu Leu Arg Gly Val Val Asp Lys
        115                 120                 125

Ile Met Ser His Tyr Glu Glu Ile Phe Lys Gln Lys Gly Asn Ala Ala
    130                 135                 140

Lys Ala Asp Val Phe His Val Leu Ser Gly Met Trp Lys Thr Pro Ala
145                 150                 155                 160

Glu Arg Cys Phe Leu Trp Leu Gly Gly Phe Arg Pro Ser Glu Leu Leu
                165                 170                 175

Lys Leu Leu Ser Thr Gln Leu Glu Pro Leu Thr Glu Gln Gln Leu Ser
            180                 185                 190

Gly Ile Ala Asn Leu Gln Gln Ser Gln Gln Ala Glu Asp Ala Leu
        195                 200                 205

Ser Gln Gly Met Glu Ala Leu Gln Gln Ser Leu Ala Glu Thr Leu Ala
    210                 215                 220

Gly Ser Leu Gly Ser Ser Gly Ser Thr Gly Asn Val Ala Asn Tyr Met
225                 230                 235                 240

Gly Gln Met Ala Met Ala Met Gly Lys Leu Gly Thr Leu Glu Asn Phe
```

```
                    245                 250                 255
Leu Arg Gln Ala Asp Asn Leu Arg Gln Gln Thr Leu Gln Gln Met Gln
            260                 265                 270

Arg Ile Leu Thr Thr Arg Gln Ser Ala Arg Ala Leu Leu Val Ile Ser
        275                 280                 285

Asp Tyr Ser Ser Arg Leu Arg Ala Leu Ser Ser Leu Trp Leu Ala Arg
    290                 295                 300

Pro Lys Glu
305

<210> SEQ ID NO 7
<211> LENGTH: 895
<212> TYPE: DNA
<213> ORGANISM: Oryza sp.
<220> FEATURE:
<221> NAME/KEY: CDS
<222> LOCATION: (2)..(895)
<223> OTHER INFORMATION: rice bZIP gene MN140

<400> SEQUENCE: 7 a cgg aga tta gcg caa aac ata gag gct gcg agg aag agc agg ctg aga      49
  Arg Arg Leu Ala Gln Asn Ile Glu Ala Ala Arg Lys Ser Arg Leu Arg
    1               5                  10                  15 aaa aag gct tat gtg caa aac cta gag acc agc agg gtc agg ctt cag       97
Lys Lys Ala Tyr Val Gln Asn Leu Glu Thr Ser Arg Val Arg Leu Gln
            20                  25                  30 cag atc gag caa gaa ctc caa aga gca cgg tca cag ggc ctg ttt ctt      145
Gln Ile Glu Gln Glu Leu Gln Arg Ala Arg Ser Gln Gly Leu Phe Leu
        35                  40                  45 ggg ggg tgc aga gca gca ggc gac atg agt tct ggc gcg gcc atg ttc      193
Gly Gly Cys Arg Ala Ala Gly Asp Met Ser Ser Gly Ala Ala Met Phe
    50                  55                  60 gac atg gag tac gcg cgc tgg ctg gac gac gac agc aag cgg ctg acc      241
Asp Met Glu Tyr Ala Arg Trp Leu Asp Asp Asp Ser Lys Arg Leu Thr
65                  70                  75                  80 gac ctc cgt ggc ggc ctg cag gcg cac ctg ctg gac acc aac ctt ggc      289
Asp Leu Arg Gly Gly Leu Gln Ala His Leu Leu Asp Thr Asn Leu Gly
                85                  90                  95 ctc atc gtg gag gag tgc atg cag cac tac gac gag ctg ttc cag ctc      337
Leu Ile Val Glu Glu Cys Met Gln His Tyr Asp Glu Leu Phe Gln Leu
            100                 105                 110 aag gcg gcg ctc gcg cgc tcc gac gtc ttc cac ctc ctc acc ggc acg      385
Lys Ala Ala Leu Ala Arg Ser Asp Val Phe His Leu Leu Thr Gly Thr
        115                 120                 125 tgg gct acc ccc gcc gag cgc tgc ttc ctc tgg atg ggc ggc ttc cgc      433
Trp Ala Thr Pro Ala Glu Arg Cys Phe Leu Trp Met Gly Gly Phe Arg
    130                 135                 140 ccc tcc gac ctt ctc aag ata ctg ata cag cag ctg gac ccg ctg acg      481
Pro Ser Asp Leu Leu Lys Ile Leu Ile Gln Gln Leu Asp Pro Leu Thr
145                 150                 155                 160 gag cag cag atg ctg ggg atc tac agc ctg cag cag tcg tcg gag cag      529
Glu Gln Gln Met Leu Gly Ile Tyr Ser Leu Gln Gln Ser Ser Glu Gln
                165                 170                 175 gcg gag gag gcg ctc gcg cag ggg ctg cag cag ctg gca cca gtc gct      577
Ala Glu Glu Ala Leu Ala Gln Gly Leu Gln Gln Leu Ala Pro Val Ala
            180                 185                 190 cgc cga cac cgt cgc cgc cgg cac gct caa cga cgg ccc cgg agt gcc      625
Arg Arg His Arg Arg Arg His Ala Gln Arg Arg Pro Arg Ser Ala
        195                 200                 205 caa cta cat gag cct cat ggc cat cgc cct gga caa gct cgc cag cct      673
```

```
Gln Leu His Glu Pro His Gly His Arg Pro Gly Gln Ala Arg Gln Pro
    210                 215                 220 cga aag ctt cta cca gca ggc tgg caa tct gag gca aca aac gtt gca        721
Arg Lys Leu Leu Pro Ala Gly Trp Gln Ser Glu Ala Thr Asn Val Ala
225                 230                 235                 240 tca gct gcg gcg gat tct aac aac ccg gca ggc ggc tcg gtg ttt cct        769
Ser Ala Ala Ala Asp Ser Asn Asn Pro Ala Gly Gly Ser Val Phe Pro
                245                 250                 255 ctc cat tgg gga gta tta ccg ccg cct ccg tgc tct cag caa cct ctg        817
Leu His Trp Gly Val Leu Pro Pro Pro Pro Cys Ser Gln Gln Pro Leu
            260                 265                 270 gtc ttc acg tcc tcg cga gaa ctt cat tgg cac cga gag cgt cag tcc        865
Val Phe Thr Ser Ser Arg Glu Leu His Trp His Arg Glu Arg Gln Ser
        275                 280                 285 cac agg aac cga gct gca acc gat gca taa                                895
His Arg Asn Arg Ala Ala Thr Asp Ala
    290                 295
```

<210> SEQ ID NO 8
<211> LENGTH: 297
<212> TYPE: PRT
<213> ORGANISM: Oryza sp.

<400> SEQUENCE: 8

```
Arg Arg Leu Ala Gln Asn Ile Glu Ala Ala Arg Lys Ser Arg Leu Arg
  1               5                  10                  15

Lys Lys Ala Tyr Val Gln Asn Leu Glu Thr Ser Arg Val Arg Leu Gln
                 20                  25                  30

Gln Ile Glu Gln Glu Leu Gln Arg Ala Arg Ser Gln Gly Leu Phe Leu
             35                  40                  45

Gly Gly Cys Arg Ala Ala Gly Asp Met Ser Ser Gly Ala Ala Met Phe
         50                  55                  60

Asp Met Glu Tyr Ala Arg Trp Leu Asp Asp Ser Lys Arg Leu Thr
 65                  70                  75                  80

Asp Leu Arg Gly Gly Leu Gln Ala His Leu Leu Asp Thr Asn Leu Gly
                 85                  90                  95

Leu Ile Val Glu Glu Cys Met Gln His Tyr Asp Glu Leu Phe Gln Leu
            100                 105                 110

Lys Ala Ala Leu Ala Arg Ser Asp Val Phe His Leu Leu Thr Gly Thr
        115                 120                 125

Trp Ala Thr Pro Ala Glu Arg Cys Phe Leu Trp Met Gly Gly Phe Arg
    130                 135                 140

Pro Ser Asp Leu Leu Lys Ile Leu Ile Gln Gln Leu Asp Pro Leu Thr
145                 150                 155                 160

Glu Gln Gln Met Leu Gly Ile Tyr Ser Leu Gln Gln Ser Ser Glu Gln
                165                 170                 175

Ala Glu Glu Ala Leu Ala Gln Gly Leu Gln Gln Leu Ala Pro Val Ala
            180                 185                 190

Arg Arg His Arg Arg Arg His Ala Gln Arg Pro Arg Ser Ala
        195                 200                 205

Gln Leu His Glu Pro His Gly His Arg Pro Gly Gln Ala Arg Gln Pro
    210                 215                 220

Arg Lys Leu Leu Pro Ala Gly Trp Gln Ser Glu Ala Thr Asn Val Ala
225                 230                 235                 240

Ser Ala Ala Ala Asp Ser Asn Asn Pro Ala Gly Gly Ser Val Phe Pro
                245                 250                 255
```

```
Leu His Trp Gly Val Leu Pro Pro Pro Cys Ser Gln Gln Pro Leu
            260                 265                 270

Val Phe Thr Ser Ser Arg Glu Leu His Trp His Arg Glu Arg Gln Ser
            275                 280                 285

His Arg Asn Arg Ala Ala Thr Asp Ala
        290                 295

<210> SEQ ID NO 9
<211> LENGTH: 1036
<212> TYPE: DNA
<213> ORGANISM: Lycopersicon sp.
<220> FEATURE:
<221> NAME/KEY: CDS
<222> LOCATION: (1)..(714)
<223> OTHER INFORMATION: carboxyl two thirds of tomato bZIP
      transcription factor NIF1 (NPR1-interacting factor 1)

<400> SEQUENCE: 9 ata gca aac atg gca gat caa tca aat gga gcg ggc gcc agt ggg acc      48
Ile Ala Asn Met Ala Asp Gln Ser Asn Gly Ala Gly Ala Ser Gly Thr
 1               5                  10                  15 tta gca ttt gat gca gaa tat agt cga tgg tta gaa gaa cac aac aaa     96
Leu Ala Phe Asp Ala Glu Tyr Ser Arg Trp Leu Glu Glu His Asn Lys
             20                  25                  30 cac atc aat gaa ttg aga acc gct gtc aat tca cat gca agt gac cct    144
His Ile Asn Glu Leu Arg Thr Ala Val Asn Ser His Ala Ser Asp Pro
         35                  40                  45 gaa ctg cga agt att gtg aat aat gtc act gca cat tac gat gag gtc    192
Glu Leu Arg Ser Ile Val Asn Asn Val Thr Ala His Tyr Asp Glu Val
     50                  55                  60 ttt agg gtg aaa gga aat gca gcc aag gca gac gta ttc cat gtc ttg    240
Phe Arg Val Lys Gly Asn Ala Ala Lys Ala Asp Val Phe His Val Leu
 65                  70                  75                  80 tca ggg atg tgg aaa acc cct gcc gag cga tgt ttt atg tgg att ggt    288
Ser Gly Met Trp Lys Thr Pro Ala Glu Arg Cys Phe Met Trp Ile Gly
                 85                  90                  95 ggc ttc cgc ccc tcg gaa ctt ctt aag ctt cta gtc aat cag ttg gag    336
Gly Phe Arg Pro Ser Glu Leu Leu Lys Leu Leu Val Asn Gln Leu Glu
            100                 105                 110 cct ctg acc gag caa cag tta gct ggc att tac aac ttg cag cag tca    384
Pro Leu Thr Glu Gln Gln Leu Ala Gly Ile Tyr Asn Leu Gln Gln Ser
        115                 120                 125 tcc cat caa gca gaa gat gcc ctt tca caa ggt atg gag gcg ttg cag    432
Ser His Gln Ala Glu Asp Ala Leu Ser Gln Gly Met Glu Ala Leu Gln
    130                 135                 140 caa tcc ttg gca gag aca tta gct aac gga tct cct gct act gaa ggg    480
Gln Ser Leu Ala Glu Thr Leu Ala Asn Gly Ser Pro Ala Thr Glu Gly
145                 150                 155                 160 tca tca gga gat gta gct aat tat atg ggt cag atg gca atg gct atg    528
Ser Ser Gly Asp Val Ala Asn Tyr Met Gly Gln Met Ala Met Ala Met
                165                 170                 175 ggg aaa tta ggg act ctt gaa ggt ttt ctc cgt cag gcg gac aac ctg    576
Gly Lys Leu Gly Thr Leu Glu Gly Phe Leu Arg Gln Ala Asp Asn Leu
            180                 185                 190 cgt caa cag aca ttg caa caa atg cat cgc ata ttg aca acc aga caa    624
Arg Gln Gln Thr Leu Gln Gln Met His Arg Ile Leu Thr Thr Arg Gln
        195                 200                 205 tca gcc cgt gct ctt ctt gca ata agt gaa tac ttc tca cgt ctt cga    672
Ser Ala Arg Ala Leu Leu Ala Ile Ser Glu Tyr Phe Ser Arg Leu Arg
    210                 215                 220 gct ctc agc tct ctt tgg ctt gcc aga cca cga gag caa taagtatgac    721
Ala Leu Ser Ser Leu Trp Leu Ala Arg Pro Arg Glu Gln
225                 230                 235
```

```
Ala Leu Ser Ser Leu Trp Leu Ala Arg Pro Arg Glu Gln
225                 230                 235 atgcattgcg atattctact gaaactcaga tatactactt cgatacactg gccggtatat    781
gagatccagc aaagttactc ttatgtataa agtggtattg tatgtgcttg tggaagtgca    841
gaatttgttt tctttctcct taggtttata gaatgccaaa attttacttt gtgacttagg    901
aaccaataat gtacctgtgt ttttagtttt acaaggaaaa agtttaggga tttttaagaa    961
gtgtaataga tattttttaga aagttttatg cttaatcaaa ttatagcttg tgactacaaa   1021
aaaaaaaaaa aaaaa                                                    1036

<210> SEQ ID NO 10
<211> LENGTH: 237
<212> TYPE: PRT
<213> ORGANISM: Lycopersicon sp.

<400> SEQUENCE: 10

Ile Ala Asn Met Ala Asp Gln Ser Asn Gly Ala Gly Ala Ser Gly Thr
1               5                   10                  15

Leu Ala Phe Asp Ala Glu Tyr Ser Arg Trp Leu Glu Glu His Asn Lys
            20                  25                  30

His Ile Asn Glu Leu Arg Thr Ala Val Asn Ser His Ala Ser Asp Pro
        35                  40                  45

Glu Leu Arg Ser Ile Val Asn Asn Val Thr Ala His Tyr Asp Glu Val
    50                  55                  60

Phe Arg Val Lys Gly Asn Ala Ala Lys Ala Asp Val Phe His Val Leu
65                  70                  75                  80

Ser Gly Met Trp Lys Thr Pro Ala Glu Arg Cys Phe Met Trp Ile Gly
                85                  90                  95

Gly Phe Arg Pro Ser Glu Leu Leu Lys Leu Leu Val Asn Gln Leu Glu
            100                 105                 110

Pro Leu Thr Glu Gln Gln Leu Ala Gly Ile Tyr Asn Leu Gln Gln Ser
        115                 120                 125

Ser His Gln Ala Glu Asp Ala Leu Ser Gln Gly Met Glu Ala Leu Gln
    130                 135                 140

Gln Ser Leu Ala Glu Thr Leu Ala Asn Gly Ser Pro Ala Thr Glu Gly
145                 150                 155                 160

Ser Ser Gly Asp Val Ala Asn Tyr Met Gly Gln Met Ala Met Ala Met
                165                 170                 175

Gly Lys Leu Gly Thr Leu Glu Gly Phe Leu Arg Gln Ala Asp Asn Leu
            180                 185                 190

Arg Gln Gln Thr Leu Gln Gln Met His Arg Ile Leu Thr Thr Arg Gln
        195                 200                 205

Ser Ala Arg Ala Leu Leu Ala Ile Ser Glu Tyr Phe Ser Arg Leu Arg
    210                 215                 220

Ala Leu Ser Ser Leu Trp Leu Ala Arg Pro Arg Glu Gln
225                 230                 235

<210> SEQ ID NO 11
<211> LENGTH: 1638
<212> TYPE: DNA
<213> ORGANISM: Arabidopsis thaliana
<220> FEATURE:
<221> NAME/KEY: CDS
<222> LOCATION: (267)..(1259)
<223> OTHER INFORMATION: bZIP transcription factor gene AHBP-1b

<400> SEQUENCE: 11
```

-continued

```
ggaatttcgg atcgtgtctc tctctgtttc tttgtttcaa tccgatttcg aatcaagccc      60
tttacttgtg caccttcaag atttcgtttt ttccagcgcc cagaatgctc cgggtgacca     120
acatttgttc ctgattcatt tcctattggt tcgtattgtc tgtgcacaca agagaaattt     180
caagaagttg ttactaaaag agaggccaca agtggatatt gtctttgtta tcaagtgtta     240
gtacagaaaa gtggtgagaa agtaat atg gct gat acc agt ccg aga act gat     293
                              Met Ala Asp Thr Ser Pro Arg Thr Asp
                                1               5 gtc tca aca gat gac gac aca gat cat cct gat ctt ggg tcg gag gga      341
Val Ser Thr Asp Asp Asp Thr Asp His Pro Asp Leu Gly Ser Glu Gly
 10              15                  20                  25 gca cta gtg aat act gct gct tct gat tcg agt gac cga tcg aag gga      389
Ala Leu Val Asn Thr Ala Ala Ser Asp Ser Ser Asp Arg Ser Lys Gly
                 30                  35                  40 aag atg gat caa aag act ctt cgt agg ctt gct caa aac cgt gag gca      437
Lys Met Asp Gln Lys Thr Leu Arg Arg Leu Ala Gln Asn Arg Glu Ala
             45                  50                  55 gca agg aaa agc aga ttg agg aag aag gct tat gtt cag cag cta gag      485
Ala Arg Lys Ser Arg Leu Arg Lys Lys Ala Tyr Val Gln Gln Leu Glu
         60                  65                  70 aac agc cgc ttg aaa cta acc cag ctt gag cag gag ctg caa aga gca      533
Asn Ser Arg Leu Lys Leu Thr Gln Leu Glu Gln Glu Leu Gln Arg Ala
     75                  80                  85 aga cag cag ggc gtc ttc att tca ggc aca gga gac cag gcc cat tct      581
Arg Gln Gln Gly Val Phe Ile Ser Gly Thr Gly Asp Gln Ala His Ser
 90                  95                 100                 105 act ggt gga aat ggt gct ttg gcg ttt gat gct gaa cat tca cgg tgg      629
Thr Gly Gly Asn Gly Ala Leu Ala Phe Asp Ala Glu His Ser Arg Trp
                110                 115                 120 ttg gaa gaa aag aac aag caa atg aac gag ctg agg tct gct ctg aat      677
Leu Glu Glu Lys Asn Lys Gln Met Asn Glu Leu Arg Ser Ala Leu Asn
            125                 130                 135 gcg cat gca ggt gat tct gag ctt cga ata ata gtc gat ggt gtg atg      725
Ala His Ala Gly Asp Ser Glu Leu Arg Ile Ile Val Asp Gly Val Met
        140                 145                 150 gct cac tat gag gag ctt ttc agg ata aag agc aat gca gct aag aat      773
Ala His Tyr Glu Glu Leu Phe Arg Ile Lys Ser Asn Ala Ala Lys Asn
    155                 160                 165 gat gtc ttt cac ttg cta tct ggc atg tgg aaa aca cca gct gag aga      821
Asp Val Phe His Leu Leu Ser Gly Met Trp Lys Thr Pro Ala Glu Arg
170                 175                 180                 185 tgt ttc ttg tgg ctc ggt gga ttt cgt tca tcc gaa ctt cta aag ctt      869
Cys Phe Leu Trp Leu Gly Gly Phe Arg Ser Ser Glu Leu Leu Lys Leu
                190                 195                 200 ctg gcg aat cag ttg gag cca atg aca gag aga cag ttg atg ggc ata      917
Leu Ala Asn Gln Leu Glu Pro Met Thr Glu Arg Gln Leu Met Gly Ile
            205                 210                 215 aat aac ctg caa cag aca tcg cag cag gct gaa gat gct ttg tct caa      965
Asn Asn Leu Gln Gln Thr Ser Gln Gln Ala Glu Asp Ala Leu Ser Gln
        220                 225                 230 ggg atg gag agc tta caa cag tca cta gct gat act tta tcg agc ggg     1013
Gly Met Glu Ser Leu Gln Gln Ser Leu Ala Asp Thr Leu Ser Ser Gly
    235                 240                 245 act ctt ggt tca agt tca tca ggg aat gtc gca agc tac atg ggt cag     1061
Thr Leu Gly Ser Ser Ser Ser Gly Asn Val Ala Ser Tyr Met Gly Gln
250                 255                 260                 265 atg gcc atg gca atg gga aag tta ggt aca ctc gaa gga ttt atc cgc     1109
Met Ala Met Ala Met Gly Lys Leu Gly Thr Leu Glu Gly Phe Ile Arg
```

-continued

```
                   270                 275                 280
cag gct gat aat ttg aga cta caa aca ttg caa cag atg ata aga gta      1157
Gln Ala Asp Asn Leu Arg Leu Gln Thr Leu Gln Gln Met Ile Arg Val
            285                 290                 295 tta aca acg aga cag tca gca cgt gct cta ctt gca ata cac gat tac      1205
Leu Thr Thr Arg Gln Ser Ala Arg Ala Leu Leu Ala Ile His Asp Tyr
        300                 305                 310 ttc tca cgg cta cga gct cta agc tcc tta tgg ctt gct cga ccc aga      1253
Phe Ser Arg Leu Arg Ala Leu Ser Ser Leu Trp Leu Ala Arg Pro Arg
    315                 320                 325 gag tgaaactgta ttttggtcac atgtcagctg tacaaaatcc atatggacac           1306
Glu
330 aaaaccagga gagactatta atcaacactt gtcagattct tcttaccaaa tccatcaaca    1366 aataagcaaa tttctgggaa acaaaagact ctttgtatgt aggtttcttc tacatggttg    1426 tggtaattca tgttgtttta gttgtagtca tcagttttta atttagcatt tgaaaagttc    1486 aatgttgttt atatagcatc ttcgattatc ttagaaaggt tattgaattt tgttttttt     1546 tgttactttt gtgtgtggta aggtgtttt aaccttgcaa cttctgtact gtaatcattt     1606 aacaatatta agatgttcta tttgagtttt gt                                  1638

<210> SEQ ID NO 12
<211> LENGTH: 330
<212> TYPE: PRT
<213> ORGANISM: Arabidopsis thaliana

<400> SEQUENCE: 12

Met Ala Asp Thr Ser Pro Arg Thr Asp Val Ser Thr Asp Asp Thr
 1               5                  10                  15

Asp His Pro Asp Leu Gly Ser Glu Gly Ala Leu Val Asn Thr Ala Ala
                20                  25                  30

Ser Asp Ser Ser Asp Arg Ser Lys Gly Lys Met Asp Gln Lys Thr Leu
            35                  40                  45

Arg Arg Leu Ala Gln Asn Arg Glu Ala Ala Arg Lys Ser Arg Leu Arg
        50                  55                  60

Lys Lys Ala Tyr Val Gln Gln Leu Glu Asn Ser Arg Leu Lys Leu Thr
 65                  70                  75                  80

Gln Leu Glu Gln Glu Leu Gln Arg Ala Arg Gln Gln Gly Val Phe Ile
                85                  90                  95

Ser Gly Thr Gly Asp Gln Ala His Ser Thr Gly Gly Asn Gly Ala Leu
            100                 105                 110

Ala Phe Asp Ala Glu His Ser Arg Trp Leu Glu Glu Lys Asn Lys Gln
        115                 120                 125

Met Asn Glu Leu Arg Ser Ala Leu Asn Ala His Ala Gly Asp Ser Glu
    130                 135                 140

Leu Arg Ile Ile Val Asp Gly Val Met Ala His Tyr Glu Glu Leu Phe
145                 150                 155                 160

Arg Ile Lys Ser Asn Ala Ala Lys Asn Asp Val Phe His Leu Leu Ser
                165                 170                 175

Gly Met Trp Lys Thr Pro Ala Glu Arg Cys Phe Leu Trp Leu Gly Gly
            180                 185                 190
```

```
Phe Arg Ser Ser Glu Leu Leu Lys Leu Leu Ala Asn Gln Leu Glu Pro
            195                 200                 205

Met Thr Glu Arg Gln Leu Met Gly Ile Asn Asn Leu Gln Gln Thr Ser
            210                 215                 220

Gln Gln Ala Glu Asp Ala Leu Ser Gln Gly Met Glu Ser Leu Gln Gln
225                 230                 235                 240

Ser Leu Ala Asp Thr Leu Ser Ser Gly Thr Leu Gly Ser Ser Ser Ser
            245                 250                 255

Gly Asn Val Ala Ser Tyr Met Gly Gln Met Ala Met Ala Met Gly Lys
            260                 265                 270

Leu Gly Thr Leu Glu Gly Phe Ile Arg Gln Ala Asp Asn Leu Arg Leu
            275                 280                 285

Gln Thr Leu Gln Gln Met Ile Arg Val Leu Thr Thr Arg Gln Ser Ala
            290                 295                 300

Arg Ala Leu Leu Ala Ile His Asp Tyr Phe Ser Arg Leu Arg Ala Leu
305                 310                 315                 320

Ser Ser Leu Trp Leu Ala Arg Pro Arg Glu
            325                 330
```

<210> SEQ ID NO 13
<211> LENGTH: 978
<212> TYPE: DNA
<213> ORGANISM: Arabidopsis thaliana
<220> FEATURE:
<221> NAME/KEY: CDS
<222> LOCATION: (1)..(978)
<223> OTHER INFORMATION: bZIP transcription factor gene TAG6

<400> SEQUENCE: 13

```
atg cat agt ttg aat gaa aca gta att cct gat gtt gat tac atg cag        48
Met His Ser Leu Asn Glu Thr Val Ile Pro Asp Val Asp Tyr Met Gln
 1               5                  10                  15 tct gat aga ggg cat atg cat gct gct gcc tct gat tcc agt gat cga        96
Ser Asp Arg Gly His Met His Ala Ala Ala Ser Asp Ser Ser Asp Arg
                20                  25                  30 tca aag gat aag ttg gat caa aag acc ctt cgt agg ctt gct caa aat       144
Ser Lys Asp Lys Leu Asp Gln Lys Thr Leu Arg Arg Leu Ala Gln Asn
            35                  40                  45 cgt gag gca gca aga aaa agc aga ttg agg aag aag gcg tat gtt cag       192
Arg Glu Ala Ala Arg Lys Ser Arg Leu Arg Lys Lys Ala Tyr Val Gln
50                  55                  60 cag ctg gaa gat agt cga tta aag ctg act caa gtt gag cag gag ctg       240
Gln Leu Glu Asp Ser Arg Leu Lys Leu Thr Gln Val Glu Gln Glu Leu
65                  70                  75                  80 caa aga gca aga cag cag gga gtt ttc atc tca agt tca gga gac caa       288
Gln Arg Ala Arg Gln Gln Gly Val Phe Ile Ser Ser Ser Gly Asp Gln
                85                  90                  95 gct cat tct act ggt ggc aat ggt ggg gct ttg gca ttt gat gca gaa       336
Ala His Ser Thr Gly Gly Asn Gly Gly Ala Leu Ala Phe Asp Ala Glu
                100                 105                 110 cac tca cga tgg ctt gaa gaa aag aac agg caa atg aac gag ctg aga       384
His Ser Arg Trp Leu Glu Glu Lys Asn Arg Gln Met Asn Glu Leu Arg
            115                 120                 125 tct gcc ctg aat gct cat gca ggt gat act gag ctc cgg ata att gtg       432
Ser Ala Leu Asn Ala His Ala Gly Asp Thr Glu Leu Arg Ile Ile Val
        130                 135                 140 gat gga gtg atg gct cac tat gag gag ctt ttc agg att aag agc aat       480
Asp Gly Val Met Ala His Tyr Glu Glu Leu Phe Arg Ile Lys Ser Asn
145                 150                 155                 160
```

```
gca tct aag aat gat gtc ttc cac ttg tta tct gga atg tgg aaa aca      528
Ala Ser Lys Asn Asp Val Phe His Leu Leu Ser Gly Met Trp Lys Thr
            165                 170                 175 cca gct gag cga tgt ttc ttg tgg ctt ggc ggg ttc ccg tca tcc gaa      576
Pro Ala Glu Arg Cys Phe Leu Trp Leu Gly Gly Phe Pro Ser Ser Glu
        180                 185                 190 ctt ctc aag ctt ctt gcg aat cag cta gag ccc atg aca gaa cga cag      624
Leu Leu Lys Leu Leu Ala Asn Gln Leu Glu Pro Met Thr Glu Arg Gln
    195                 200                 205 gta atg ggc atc aat agc ttg cag cag acg tcg cag cag gca gaa gat      672
Val Met Gly Ile Asn Ser Leu Gln Gln Thr Ser Gln Gln Ala Glu Asp
210                 215                 220 gct tta tct caa ggg atg gag agt tta cag caa tcc cta gct gat act      720
Ala Leu Ser Gln Gly Met Glu Ser Leu Gln Gln Ser Leu Ala Asp Thr
225                 230                 235                 240 tta tcc agt gga act ctt ggt tcc agt tca tcg gat aat gtc gcg agc      768
Leu Ser Ser Gly Thr Leu Gly Ser Ser Ser Asp Asn Val Ala Ser
            245                 250                 255 tac atg ggt cag atg gcc atg gca atg ggc aag tta ggc acc ctc gaa      816
Tyr Met Gly Gln Met Ala Met Ala Met Gly Lys Leu Gly Thr Leu Glu
        260                 265                 270 gga ttc ata cgc cag gct gat aac ttg agg ctg caa aca cta caa cag      864
Gly Phe Ile Arg Gln Ala Asp Asn Leu Arg Leu Gln Thr Leu Gln Gln
    275                 280                 285 atg ctt cga gta tta aca aca cgt cag tca gct cgt gct ctt ctt gct      912
Met Leu Arg Val Leu Thr Thr Arg Gln Ser Ala Arg Ala Leu Leu Ala
290                 295                 300 ata cac gat tat tca tct cga tta cgt gct ctt agt tcc ttg tgg ctt      960
Ile His Asp Tyr Ser Ser Arg Leu Arg Ala Leu Ser Ser Leu Trp Leu
305                 310                 315                 320 gcc cgg cca aga gag tga                                              978
Ala Arg Pro Arg Glu
            325

<210> SEQ ID NO 14
<211> LENGTH: 325
<212> TYPE: PRT
<213> ORGANISM: Arabidopsis thaliana

<400> SEQUENCE: 14

Met His Ser Leu Asn Glu Thr Val Ile Pro Asp Val Asp Tyr Met Gln
 1               5                  10                  15

Ser Asp Arg Gly His Met His Ala Ala Ser Asp Ser Ser Asp Arg
            20                  25                  30

Ser Lys Asp Lys Leu Asp Gln Lys Thr Leu Arg Arg Leu Ala Gln Asn
        35                  40                  45

Arg Glu Ala Ala Arg Lys Ser Arg Leu Arg Lys Lys Ala Tyr Val Gln
    50                  55                  60

Gln Leu Glu Asp Ser Arg Leu Lys Leu Thr Gln Val Glu Gln Glu Leu
65                  70                  75                  80

Gln Arg Ala Arg Gln Gln Gly Val Phe Ile Ser Ser Gly Asp Gln
            85                  90                  95

Ala His Ser Thr Gly Gly Asn Gly Gly Ala Leu Ala Phe Asp Ala Glu
        100                 105                 110

His Ser Arg Trp Leu Glu Glu Lys Asn Arg Gln Met Asn Glu Leu Arg
    115                 120                 125

Ser Ala Leu Asn Ala His Ala Gly Asp Thr Glu Leu Arg Ile Ile Val
130                 135                 140
```

```
Asp Gly Val Met Ala His Tyr Glu Glu Leu Phe Arg Ile Lys Ser Asn
145                 150                 155                 160

Ala Ser Lys Asn Asp Val Phe His Leu Leu Ser Gly Met Trp Lys Thr
                165                 170                 175

Pro Ala Glu Arg Cys Phe Leu Trp Leu Gly Gly Phe Pro Ser Ser Glu
            180                 185                 190

Leu Leu Lys Leu Leu Ala Asn Gln Leu Glu Pro Met Thr Glu Arg Gln
        195                 200                 205

Val Met Gly Ile Asn Ser Leu Gln Gln Thr Ser Gln Gln Ala Glu Asp
    210                 215                 220

Ala Leu Ser Gln Gly Met Glu Ser Leu Gln Gln Ser Leu Ala Asp Thr
225                 230                 235                 240

Leu Ser Ser Gly Thr Leu Gly Ser Ser Ser Asp Asn Val Ala Ser
                245                 250                 255

Tyr Met Gly Gln Met Ala Met Ala Met Gly Lys Leu Gly Thr Leu Glu
            260                 265                 270

Gly Phe Ile Arg Gln Ala Asp Asn Leu Arg Leu Gln Thr Leu Gln Gln
        275                 280                 285

Met Leu Arg Val Leu Thr Thr Arg Gln Ser Ala Arg Ala Leu Leu Ala
    290                 295                 300

Ile His Asp Tyr Ser Ser Arg Leu Arg Ala Leu Ser Ser Leu Trp Leu
305                 310                 315                 320

Ala Arg Pro Arg Glu
                325

<210> SEQ ID NO 15
<211> LENGTH: 1111
<212> TYPE: DNA
<213> ORGANISM: Arabidopsis thaliana
<220> FEATURE:
<221> NAME/KEY: CDS
<222> LOCATION: (1)..(993)
<223> OTHER INFORMATION: bZIP transcription factor gene OBF5

<400> SEQUENCE: 15 atg gga gat act agt cca aga aca tca gtc tca aca gat gga gac act      48
Met Gly Asp Thr Ser Pro Arg Thr Ser Val Ser Thr Asp Gly Asp Thr
 1               5                  10                  15 gat cat aat aac cta atg ttc gat gaa ggg cat ttg ggt atc ggt gct      96
Asp His Asn Asn Leu Met Phe Asp Glu Gly His Leu Gly Ile Gly Ala
                20                  25                  30 tct gat tct agt gac cgt tca aag agt aaa atg gat caa aag acg ctt     144
Ser Asp Ser Ser Asp Arg Ser Lys Ser Lys Met Asp Gln Lys Thr Leu
            35                  40                  45 cgt agg ctc gct caa aac cgt gag gct gca agg aaa agc aga ttg agg     192
Arg Arg Leu Ala Gln Asn Arg Glu Ala Ala Arg Lys Ser Arg Leu Arg
        50                  55                  60 aag aaa gca tat gtt cag cag cta gag aac agt cga ttg aag cta aca     240
Lys Lys Ala Tyr Val Gln Gln Leu Glu Asn Ser Arg Leu Lys Leu Thr
 65                  70                  75                  80 caa ctt gag cag gag cta caa aga gca cgg caa cag ggt gtc ttt atc     288
Gln Leu Glu Gln Glu Leu Gln Arg Ala Arg Gln Gln Gly Val Phe Ile
                85                  90                  95 tca agc tct gga gac caa gcc cat tct acc gct gga gat ggg gca atg     336
Ser Ser Ser Gly Asp Gln Ala His Ser Thr Ala Gly Asp Gly Ala Met
            100                 105                 110 gca ttt gat gta gaa tac aga cga tgg cag gaa gat aaa aac aga cag     384
Ala Phe Asp Val Glu Tyr Arg Arg Trp Gln Glu Asp Lys Asn Arg Gln
        115                 120                 125
```

```
atg aag gag ctg agt tct gct ata gat tct cac gcg act gat tct gag       432
Met Lys Glu Leu Ser Ser Ala Ile Asp Ser His Ala Thr Asp Ser Glu
    130                 135                 140 ctt cgg ata att gta gat gga gta ata gct cac tat gag gag ctt tac       480
Leu Arg Ile Ile Val Asp Gly Val Ile Ala His Tyr Glu Glu Leu Tyr
145                 150                 155                 160 agg ata aaa ggc aac gca gct aag agt gat gtc ttc cat tta tta tca       528
Arg Ile Lys Gly Asn Ala Ala Lys Ser Asp Val Phe His Leu Leu Ser
                165                 170                 175 ggg atg tgg aaa acc cca gct gag aga tgt ttc ttg tgg ctc ggc ggt       576
Gly Met Trp Lys Thr Pro Ala Glu Arg Cys Phe Leu Trp Leu Gly Gly
            180                 185                 190 ttc cgt tca tca gaa ctt ctc aag ctt ata gcg tgt cag ttg gag ccc       624
Phe Arg Ser Ser Glu Leu Leu Lys Leu Ile Ala Cys Gln Leu Glu Pro
        195                 200                 205 ttg aca gaa caa caa tcg cta gac ata aat aac ttg caa cag tca act       672
Leu Thr Glu Gln Gln Ser Leu Asp Ile Asn Asn Leu Gln Gln Ser Thr
    210                 215                 220 cag caa gca gaa gat gct ttg tct caa ggg atg gac aac tta cag caa       720
Gln Gln Ala Glu Asp Ala Leu Ser Gln Gly Met Asp Asn Leu Gln Gln
225                 230                 235                 240 tca ctc gct gat act tta tcg agt ggg act ctc ggt tca agt tca tca       768
Ser Leu Ala Asp Thr Leu Ser Ser Gly Thr Leu Gly Ser Ser Ser Ser
                245                 250                 255 ggg aat gta gct agc tac atg ggt cag atg gcc atg gcg atg ggg aag       816
Gly Asn Val Ala Ser Tyr Met Gly Gln Met Ala Met Ala Met Gly Lys
            260                 265                 270 tta ggt acc ctt gaa gga ttt atc cgc cag gct gat aac tta agg cta       864
Leu Gly Thr Leu Glu Gly Phe Ile Arg Gln Ala Asp Asn Leu Arg Leu
        275                 280                 285 caa aca tat caa cag atg gtg aga cta tta aca acc cga caa tcg gct       912
Gln Thr Tyr Gln Gln Met Val Arg Leu Leu Thr Thr Arg Gln Ser Ala
    290                 295                 300 cgt gct ctc ctt gca gta cac aat tat aca ttg cgg tta cgt gct ctt       960
Arg Ala Leu Leu Ala Val His Asn Tyr Thr Leu Arg Leu Arg Ala Leu
305                 310                 315                 320 agc tct cta tgg ctt gcc aga cca aga gag tgaaccatga ctctattata       1010
Ser Ser Leu Trp Leu Ala Arg Pro Arg Glu
                325                 330 cttcaacgaa ggtccagaaa atttgagatt cttagcataa gatttgacga ctttagacac    1070
gtagctcgta tacaagatta tgattatact gttttgtgtt g                        1111

<210> SEQ ID NO 16
<211> LENGTH: 330
<212> TYPE: PRT
<213> ORGANISM: Arabidopsis thaliana

<400> SEQUENCE: 16

Met Gly Asp Thr Ser Pro Arg Thr Ser Val Ser Thr Asp Gly Asp Thr
 1               5                  10                  15

Asp His Asn Asn Leu Met Phe Asp Glu Gly His Leu Gly Ile Gly Ala
            20                  25                  30

Ser Asp Ser Ser Asp Arg Ser Lys Ser Lys Met Asp Gln Lys Thr Leu
        35                  40                  45

Arg Arg Leu Ala Gln Asn Arg Glu Ala Ala Arg Lys Ser Arg Leu Arg
    50                  55                  60

Lys Lys Ala Tyr Val Gln Gln Leu Glu Asn Ser Arg Leu Lys Leu Thr
65                  70                  75                  80
```

Gln Leu Glu Gln Glu Leu Gln Arg Ala Arg Gln Gln Gly Val Phe Ile
                85                  90                  95

Ser Ser Ser Gly Asp Gln Ala His Ser Thr Ala Gly Asp Gly Ala Met
        100                 105                 110

Ala Phe Asp Val Glu Tyr Arg Arg Trp Gln Glu Asp Lys Asn Arg Gln
        115                 120                 125

Met Lys Glu Leu Ser Ser Ala Ile Asp Ser His Ala Thr Asp Ser Glu
    130                 135                 140

Leu Arg Ile Ile Val Asp Gly Val Ile Ala His Tyr Glu Glu Leu Tyr
145                 150                 155                 160

Arg Ile Lys Gly Asn Ala Ala Lys Ser Asp Val Phe His Leu Leu Ser
                165                 170                 175

Gly Met Trp Lys Thr Pro Ala Glu Arg Cys Phe Leu Trp Leu Gly Gly
            180                 185                 190

Phe Arg Ser Ser Glu Leu Leu Lys Leu Ile Ala Cys Gln Leu Glu Pro
        195                 200                 205

Leu Thr Glu Gln Gln Ser Leu Asp Ile Asn Asn Leu Gln Gln Ser Thr
    210                 215                 220

Gln Gln Ala Glu Asp Ala Leu Ser Gln Gly Met Asp Asn Leu Gln Gln
225                 230                 235                 240

Ser Leu Ala Asp Thr Leu Ser Ser Gly Thr Leu Gly Ser Ser Ser Ser
                245                 250                 255

Gly Asn Val Ala Ser Tyr Met Gly Gln Met Ala Met Ala Met Gly Lys
            260                 265                 270

Leu Gly Thr Leu Glu Gly Phe Ile Arg Gln Ala Asp Asn Leu Arg Leu
        275                 280                 285

Gln Thr Tyr Gln Gln Met Val Arg Leu Leu Thr Thr Arg Gln Ser Ala
    290                 295                 300

Arg Ala Leu Leu Ala Val His Asn Tyr Thr Leu Arg Leu Arg Ala Leu
305                 310                 315                 320

Ser Ser Leu Trp Leu Ala Arg Pro Arg Glu
                325                 330

<210> SEQ ID NO 17
<211> LENGTH: 19
<212> TYPE: DNA
<213> ORGANISM: Cauliflower mosaic virus
<220> FEATURE:
<223> OTHER INFORMATION: CaMV 35S promoter ocs consensus element
      salicylic acid responsive element

<400> SEQUENCE: 17
tgacgtaagc gcttagtca                                              19

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence:(His)6-tag

<400> SEQUENCE: 18

His His His His His His
 1               5

<210> SEQ ID NO 19
<211> LENGTH: 33
<212> TYPE: DNA

```
<213> ORGANISM: Artificial Sequence
<220> FEATURE:
<223> OTHER INFORMATION: Description of Artificial Sequence:gel
      mobility shift assay wild-type oligonucleotide probe

<400> SEQUENCE: 19
ctctacgtca ctattttact tacgtcatag atg                          33

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence:gel
      mobility shift assay mutant oligonucleotide probe

<400> SEQUENCE: 20
ctctattcta ctattttact tattctatag atg                          33

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence:primary
      PCR reaction anchor primer SS20

<400> SEQUENCE: 21
agggatgttt aataccacta c                                       21

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence:primary PCR
      reaction gene-specific primer mn1-1

<400> SEQUENCE: 22
gaagccatga ctgcacca                                           18

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence:primary PCR
      reaction gene-specific primer mn8-1

<400> SEQUENCE: 23
ttatcgtcgg tatccagga                                          19

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence:secondary PCR
      reaction anchor primer

<400> SEQUENCE: 24
acccgggaga gatcgaattc ggcacga                                 27

<210> SEQ ID NO 25
<211> LENGTH: 19
<212> TYPE: DNA
<213> ORGANISM: Artificial Sequence
```

```
-continued

<220> FEATURE:
<223> OTHER INFORMATION: Description of Artificial Sequence:secondary PCR
      reaction gene-specific primer mn1-2

<400> SEQUENCE: 25
caccactatg tccgttttc                                                    19

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence:secondary
      PCR reaction gene-specific primer mn8-2

<400> SEQUENCE: 26
ggactgttga tgtgtcagt                                                    19
```

DNA BINDING PROTEINS THAT INTERACT WITH NPR1

This invention was made with Government support under Grant No. MCB9728111 awarded by the National Science Foundation. The Government has certain rights in the invention.

BACKGROUND OF THE INVENTION

Plant pathogens cause hundreds of millions of dollars in damage to crops in the United States annually and cause significantly more damage worldwide. Traditional plant breeding techniques have developed some plants that resist specific pathogens, but these techniques are limited to genetic transfer within breeding species and can be plagued with the difficulty of introducing non-agronomic traits that are linked to pathogen resistance. Furthermore, traditional breeding has focused on resistance to specific pathogens rather than general, or systemic, resistance to a wide spectrum of pathogens. Therefore, an important goal in agriculture is to identify genetic components that enable plants to resist pathogens, thereby allowing for the development of systemically resistant plants through biotechnology.

Systemic acquired resistance (SAR) is a general plant resistance response that can be induced during a local infection by an avirulent pathogen. While early studies of SAR were conducted using tobacco mosaic virus (TMV) and its Solanaceous hosts (see, e.g., Ross, A. F. *Virology* 14: 340–358 (1961)), SAR has been demonstrated in many plant species and shown to be effective against not only viruses, but also bacterial and fungal pathogens (see, e.g., Kuc, *J. Bioscience* 32:854–860 (1982) and Ryals, et al., *Plant Cell* 8:1809–1819 (1996)). A necessary signal for SAR induction is salicylic acid (SA); plants that fail to accumulate SA due to the expression of an SA-oxidizing enzyme salicylate hydroxylase are impaired in SAR (Gaffney, T., et al. *Science* 261:754–756 (1993)). Conversely, an elevation in the endogenous level of SA or exogenous application of SA or its synthetic analogs, such as 2,6-dichloroisonicotinic acid (INA), not only results in an enhanced, broad-spectrum resistance but also stimulates concerted expression of a battery of genes known as pathogenesis-related (PR) genes (see, e.g., Malamy, J., et al. *Science* 250:1002–1004 (1990); Métraux, J.-P., et al. *Science* 250:1004–1006 (1990); Rasmussen, J. B., et al. *Plant Physiol* 97:1342–1347 (1991); Yalpani, N., et al. *Plant Cell* 3:809–818 (1991); White, R. F. *Virology* 99:410–412 (1979); Métraux, J.-P., et al. (1991) In *Advances in Molecular Genetics of Plant-Microbe Interactions*, eds. Hennecke, H. & Verma, D. P. S. (Kluwer Academic, Dordrechet, The Netherlands), Vol. 1, pp. 432–439; Ward et al. *Plant Cell* 3:1085–1094 (1991); and Uknes et al. *Plant Cell* 4:645–656 (1992)). PR genes may play direct roles in conferring resistance because their expression coincides with the onset of SAR and some of the PR genes encode enzymes with antimicrobial activities (see, e.g., Ward et al. *Plant Cell* 3:1085–1094 (1991); and Uknes et al. *Plant Cell* 4:645–656 (1992)). Therefore, understanding the regulation of PR gene expression has been a focal point of research in plant disease resistance.

Two classes of *A. thaliana* mutants with altered PR gene expression have been identified. One class constitutively expresses PR genes while the other class is impaired in the SA- or INA-induced PR gene expression (Lawton, K., et al. (1993) in *Mechanisms of Defense Responses in Plants*, eds. Fritig, B. & Legrand, M. (Kluwer Academic, Dordrecht, The Netherlands), pp. 422–432; Bowling, S. A., et al. *Plant Cell* 6:1845–1857 (1994); Bowling, S. A., et al. *Plant Cell* 9:1573–1584 (1997); Clarke, J. D., et al. *Plant Cell* 10:57–569 (1998); Cao, H., et al. *Plant Cell* 6:583–1592 (1994); Delaney, T. P., et al. *Proc. Natl. Acad. Sci. USA* 92:602–6606 (1995); Glazebrook, J., et al., *Genetics* 143, 973–982 (1996); Shah, J., et al. *Mol. Plant-Microbe. Interact.* 10:69–78 (1997)). Interestingly, from the second class of mutants only one genetic locus, NPR1 (also known as NIM1), has been identified. NPR1 has been shown to be a key component of the SA-regulated PR gene expression and disease resistance because nprl mutants fail to express PR1, PR2, and PR5 and display enhanced susceptibility to infection even after treatment with SA or INA. Furthermore, transgenic plants overexpressing NPR1 display a more dramatic induction of PR genes during an infection and show complete resistance to *Pseudomonas syringae* pv. *maculicola* 4326 and *Peronospora parasitica* Noco, two very different pathogens that are virulent on wild-type A. thaliana plants (Cao, H., et al. *Proc. Natl. Acad. Sci. USA* 95:6531–6536 (1998)).

Sequence analysis of NPR1 does not reveal any obvious homology to known transcription factors (see, e.g., Cao, H., et al. *Cell* 88:57–63 (1997) and Ryals, J. A., et al. *Plant Cell* 9:425–439 (1997)). Therefore, it is unlikely that NPR1 is directly involved in transactivating the promoters of PR genes. However, NPR1 contains at least four ankyrin repeats, which are found in proteins with very diverse biological functions and are involved in protein-protein interactions (Bork, P. (1993) *Proteins: Structure, Function, and Genetics* 17, 363–374. Michaely, P., and Bennet, V. (1992) *Trends in Cell Biology* 2:127–129.). The functional importance of the ankyrin repeat domain has been demonstrated by mutations found in the npr1-1 and the nim1-2 alleles where the highly conserved histidine residues in the third and the second ankyrn repeats, respectively, are changed to a tyrosine. Because these conserved histidine residues are involved in the formation of hydrogen bonds which are crucial in stabilizing the three dimensional structure of the ankyrin-repeat domain (Gorina, S. & Pavletich, N. P. *Science* 274, 1001–1005 (1996)), npr1-1 and nim1-2 mutations may cause disruption in the local structure within the ankyrin-repeat domain and abolish its ability to interact with other proteins. These data suggest that NPR1 probably exerts its regulatory function by interacting with other proteins.

SA-responsive promoter elements such as the as-1 element in the 35S promoter of cauliflower mosaic virus (CaMV) and the ocs and nos elements in opine synthase promoters of Agrobacterium have previously been identified and characterized (Lam, E., et al. *Proc. Natl. Acad. Sci. USA* 86, 7890–7894 (1989); Qin, X-F., et al. *Plant Cell* 6, 863–874 (1994) ; and Ellis, J. G., et al. *Plant J.* 4, 433–443 (1993)). The as-1 element has been shown to bind to a tobacco transcription factor, SARP (salicylic acid response protein), which is immunologically related to the tobacco protein TGA1a, a bZIP transcription factor (Jupin, I. & Chua N-H. (1996) *EMBO J.* 15:5679–5689). In *A. thaliana*, there are at least six bZIP genes identified that have homology to the tobacco TGA transcription factor (Kawata, T., et al. *Nucleic Acids Res.* 20, 1141 (1992); Xiang, C., et al. *Plant Mol. Biol.* 34, 403–415 (1997); Zhang, B., et al. *Plant J.* 4,711–716 (1993 ); Schindler, U., et al., A. R. *Plant Cell* 4, 1309–1319 (1992); Miao, Z. H., et al. *Plant Mol. Biol.* 25, 1–11 (1994); and Lam, E. & Lam, Y. K.-P. *Nucleic Acids Res.* 23, 3778–3785 (1995)). These TAG transcription factors have been shown to have different affinities for the as-1 element in in vitro binding assays (Lam, E. & Lam, Y. K.-P.

*Nucleic Acids Res.* 23, 3778–3785 (1995)). While strong, binding of AHBP-1b requires two tandem copies of the TGACG motif present in the as-1 element, binding of TGA6 appears to be unaffected by the number of motifs because a single copy seems to be sufficient. Other bZIP genes have been identified in wheat (see, e.g., Foley et al., *Plant J.* 3(5):669–79 (1993) and tobacco (see, e.g., Fromm, et al, *Mol. Gen. Genet.* 229:181–88 (1991) and Katagiri et al., *Nature* 340:727–30 (1989)). Although functions have been postulated for some of the above-described bZIP gene products, little is known about the regulation of bZIP gene products and there are no reports of their interaction with any other proteins associated with plant disease resistance.

Recently, the promoter of the *A. thaliana* PR-1 gene has been thoroughly analyzed using deletion and linker scanning mutagenesis performed in transgenic plants as well as in vivo footprinting analysis (Lebel, E., et al. *Plant J.* 16, 223–234 (1998)). Through these analyses, two INA-responsive elements have been defined. One element at −610 is similar to a recognition sequence for the transcription factor NF-κB, while the other promoter element around residue −640 contains a CGTCA motif (the complementary sequence is TGACG) which is present in the as-1 element. The CGTCA motif was shown by linker-scanning mutagenesis to be essential for both SA and INA induction of PR-1 gene expression.

In spite of the recent progress in understanding the genetic control of plant resistance to pathogens, little progress has been reported in the identification and analysis of genes interacting with key regulators of pathogen resistance such as NPR1. Characterization of such genes would allow for the genetic engineering of plants with a variety of desirable traits. The present invention addresses these and other needs.

SUMMARY OF THE INVENTION

This invention relates to bZIP polynucleotides and polypeptides that bind to NPR1, as well as the use of such polynucleotides and polypeptides to generate transgenic plants that have enhanced resistance to plant pathogens. For example, the invention provides molecular strategies for enhancing resistance to pathogens by modulating bZIP expression and activity using bZIP gene constructs. Thus, by regulating bZIP expression, transgenic plants with increased or decreased pathogen resistance can be produced.

The present invention provides for isolated nucleic acids comprising a polynucleotide that is at least 95% identical over at least 500 base pairs to SEQ ID NO:1, SEQ ID NO:3, SEQ ID NO:5, SEQ ID NO:7 or SEQ ID NO:9. The isolated nucleic acids can be derived, for instance, from rice or tomato. In preferred embodiments, the polynucleotide encodes SEQ ID NO:2, SEQ ID NO:4, SEQ ID NO:6, SEQ ID NO:8 or SEQ ID NO:10.

The invention also provides for transgenic plants comprising a recombinant expression cassette comprising a plant promoter operably linked to a polynucleotide that is at least 95% identical over at least 500 base pairs to SEQ ID NO:1, SEQ ID NO:3, SEQ ID NO:5, SEQ ID NO:7 or SEQ ID NO:9 and that encodes a polypeptide capable of interacting with NPR1.

A promoter can be operably linked to the polynucleotide sequence. The plant promoters used in the invention are not critical to the invention. The promoter can be constitutive, inducible or specific for an organ, tissue, or cell.

The present invention also provides for methods of enhancing plant resistance to pathogens by introducing into a plant a recombinant expression cassette with a plant promoter operably linked to a bZIP polynucleotide sequence and selecting for a plant with enhanced resistance. In one embodiment, the method is performed on rice or tomato plants. In another embodiment, plant resistance is determined by measuring for increased expression from a defense-related promoter. In preferred embodiments of this method, the bZIP polynucleotide encodes SEQ ID NO:2, SEQ ID NO:4, SEQ ID NO:6, SEQ ID NO:8 or SEQ ID NO:10. In other preferred embodiments, the bZIP polynucleotide of the method are SEQ ID NO:1, SEQ ID NO:3, SEQ ID NO:5, SEQ ID NO:7 or SEQ ID NO:9.

The invention also provides a method of identifying other polypeptides that are involved in plant disease resistance. The method comprises identifying a polypeptide that binds to NPR1 and determining whether the identified polypeptide modulates disease resistance. In some embodiments, the determining step comprises determining whether the identified polypeptide modulates expression of at least one defense-related gene. Preferably the defense related gene encodes a pathogenesis-related protein. In another preferred embodiment, the determining step comprises introducing into a plant a polynucleotide that encodes the identified polypeptide. In yet other embodiments, the polypeptide used in the method is derived from tomato or rice.

Definitions

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

The term "promoter" refers to regions or sequence located upstream and/or downstream from the start of transcription and which are involved in recognition and binding of RNA polymerase and other proteins to initiate transcription. A "plant promoter" is a promoter capable of initiating transcription in plant cells.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichornes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

"Increased or enhanced bZIP activity or expression of the bZIP gene" refers to an augmented change in bZIP activity. Examples of such increased activity or expression include the following. BZIP activity or expression of the bZIP gene is increased above the level of that in wild-type, non-transgenic control plants (i.e. the quantity of bZIP activity or expression of the bZIP gene is increased). BZIP activity or expression of the bZIP gene is in an organ, tissue or cell where it is not normally detected in wild-type, non-transgenic control plants (i.e. spatial distribution of bZIP activity or expression of the bZIP gene is increased). BZIP activity or expression is increased when bZIP activity or expression of the bZIP gene is present in an organ, tissue or cell for a longer period than in a wild-type, non-transgenic controls (i.e. duration of bZIP activity or expression of the bZIP gene is increased).

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety).

"Recombinant" refers to a human manipulated polynucleotide or a copy or complement of a human manipulated polynucleotide. For instance, a recombinant expression cassette comprising a promoter operably linked to a second polynucleotide may include a promoter that is heterologous to the second polynucleotide as the result of human manipulation (e.g., by methods described in Sambrook et al., *Molecular Cloning-A Laboratory Manual*, Cold Spring Harbor Laboratory, Cold Spring Harbor, New York, (1989) or Current Protocols in Molecular Biology Volumes 1–3, John Wiley & Sons, Inc. (1994–1998)) of an isolated nucleic acid comprising the expression cassette. In another example, a recombinant expression cassette may comprise polynucleotides combined in such a way that the polynucleotides are extremely unlikely to be found in nature. For instance, human manipulated restriction sites or plasmid vector sequences may flank or separate the promoter from the second polynucleotide. One of skill will recognize that polynucleotides can be manipulated in many ways and are not limited to the examples above.

A polynucleotide "exogenous to" an individual plant is a polynucleotide which is introduced into the plant by any means other than by a sexual cross. Examples of means by which this can be accomplished are described below, and include Agrobacterium-mediated transformation, biolistic methods, electroporation, and the like. Such a plant containing the exogenous nucleic acid is referred to here as a $T_1$ (e.g. in Arabidopsis by vacuum infiltration) or $R_0$ (for plants regenerated from transformed cells in vitro) generation transgenic plant. Transgenic plants that arise from sexual cross or by selfing are descendants of such a plant.

A "bZIP nucleic acid" or "bZIP polynucleotide sequence" of the invention is a subsequence or full length polynucleotide sequence (e.g., SEQ ID NO:1, SEQ ID NO:3, SEQ ID NO:5, SEQ ID NO:7, SEQ ID NO:9) which encodes a polypeptide (e.g., SEQ ID NO:2, SEQ ID NO:4, SEQ ID NO:6, SEQ ID NO:8, SEQ ID NO:10) or its complement. BZIP polypeptides of the invention are characterized by the presence of a leucine zipper domain and a basic domain (see, e.g., Baranger, *Curr. Opin. Chem. Biol.* 2(1):18–23 (1998); Xiang, et al., *Plant Mol. Biol.* 34:403–15 (1997); and Ramachandran et al., *Curr. Opin. Genet. Dev.* 4:642–46 (1994)). The leucine zipper domain can function to dimerize with other proteins (see, e.g., Vinson et al., *Science* 246:911–16 (1989)). BZIP proteins can therefore form hetero- and homodimers, allowing for different DNA or protein specificities. The basic domain of a bZIP protein is the region of the polypeptide that binds to DNA. BZIP polynucleotides of the invention are preferably at least 95% identical, more preferably at least 97% identical and most preferably at least 99% identical over at least 500 base pairs to SEQ ID NO:1, SEQ ID NO:3, SEQ ID NO:5, SEQ ID NO:7, SEQ ID NO:9.

BZIP polypeptides of the invention interact with NPR1. This interaction can be by direct protein-protein interaction. Alternatively, the interaction may be indirect. For instance, a third polypeptide may bind to both the bZIP polypeptide and NPR1, thereby keeping all three polypeptides in proximity to one another. Protein interactions can be measured by a number of different methods that are known to those of ordinary skill in the art. Examples of systems to measure such interaction include, inter alia, the yeast two-hybrid system (see, e.g., Fields, *Nature* 340(6230):245–6 (1989) and Finley, R. L. JR & Brent R. (1996) in DNA *Cloning— Expression Systems: A Practical Approach*, eds. Glover D. & Hames B. D (Oxford University Press, Oxford, England), pp. 169–203), immunoprecipitation (see, e.g., Current Protocols in Molecular Biology Volumes 2, §10.16, John Wiley & Sons, Inc. (1994–1998)), or the use of various sequence tags (e.g., TAG, His, etc.) that allow for the isolation of a polypeptide under nondenaturing conditions (see, e.g., Chen & Hai *Gene* 139(1):73–5 (1994); and Current Protocols in Molecular Biology Volumes 2, §§10.1A–B, 10.15, John Wiley & Sons, Inc. (1994–1998)). These methods can therefore be used to identify proteins that interact with NPR1. One of ordinary skill in the art will recognize that protein-protein interactions can be measured by any number of methods and are not limited to those described above.

In the case of both expression of transgenes and inhibition of endogenous genes (e.g., by antisense, or co-suppression) one of skill will recognize that the inserted polynucleotide sequence need not be identical, but may be only "substantially identical" to a sequence of the gene from which it was derived. As explained below, these substantially identical variants are specifically covered by the term bZIP nucleic acid.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the terms "bZIP nucleic acid", "bZIP polynucleotide" and their equivalents. In addition, the terms specifically include those full length sequences substantially identical (determined as described below) with an bZIP polynucleotide sequence and that encode proteins that retain the function of the bZIP polypeptide (e.g., resulting from conservative substitutions of amino acids in the bZIP polypeptide).

An "NPR1 polynucleotide sequence" of the invention is a subsequence or full length polynucleotide sequence which, encodes a polypeptide or its complement, as described, for instance, by Cao, H., et al. *Cell* 88(1):57– 63 (1997) and Ryals, J. A., et al. *Plant Cell* 9:425–439 (1997) (see, also, GenBank Accession Nos. U76707 and U87794). One of ordinary skill in the art will recognize that NPR1 also encompasses any orthologs of NPR1 from different plant species. For instance, as described below, the tomato NPR1 gene is an NPR1 ortholog and therefore is an "NPR1 polynucleotide" of the invention.

A "salicylic acid (SA) responsive element" is a cis-acting DNA sequence that modulates a particular gene's expression in response to exposure of a plant or part of a plant to salicylic acid, salicylate, or any chemical capable of inducing systemic acquired resistance in plants e.g., acetylsalicylic acid or 2,6 dichloroisonicotinic acid (see, e.g., Ward, et al. *Plant Cell* 3:1085–1094 (1991)). Known SA-responsive promoter elements include, for example, the as-1 element in the 35S promoter of cauliflower mosaic virus (CaMV) and the ocs-1 and nos elements in opine synthase promoters of Agrobacterium (see, e.g., Lam, E., et al. *Proc. Natl. Acad. Sci. USA* 86:7890–7894 (1989); Qin, X-F., et al. *Plant Cell* 6:863–874 (1994); and Ellis, J. G., et al. *Plant J.* 4:433–443 (1993)). A motif that arises in many SA responsive elements is TGACG (or its complement CGTCA). For example, the CaMV 35S promoter contains the as-1 element, identified as a 21 bp DNA sequence that comprises the sequence TGACG (see, e.g., Qin, et al., *Plant Cell* 6:863–74 (1994); Xiang, C., et al. *Plant Mol. Biol.* 34:403–415 (1997)). The hex element, another SA responsive element, also comprises the TGACG sequence (Xiang, C., et al. *Plant Mol. Biol.* 34:403–415 (1997); Katagiri et al., *Nature* 340:727–30 (1989)). Similarly, the nos-1 element of the CaMV 35S promoter also comprises the TGACG motif and plays a role in controlling gene expression in response to exposure of a plant to salicylic acid (see, e.g., Lam, et al. *J Biol Chem* 265(17):9909–13 (1990) and Kim et al. *Plant Mol Biol* 124(1):105–17 (1994)). Another SA responsive element is the ocs element of the CaMV 35S promoter. The ocs consensus element is TGACGTAAGCGCTTAGTCA (SEQ ID NO:17) (see, e.g., Zhang, B., et al. *Plant J.* 4, 711–716 (1993)) and represents a family of ocs elements found in higher plants (see, e.g., Bouchez, et al., *EMBO J.* 8:4197–204 (1989)). One potential binding site of bZIP proteins within the ocs sequence comprises the motif(A) CGTCA (see, e.g., Lebel etal., *Plant J.* 16(2):223–233 (1998) and Rushton et al., *EMBO J.* 15:5690–5700 (1996)). Additional examples of SA-responsive elements are discussed, inter alia, in Stange, et al. *Plant J.* 11(6): 1315–24 (1997); Horvath et al. *Mol Plant Microbe Interact.* 11(9):895–905 (1998); and Ulmasov, et al. *Plant Mol Biol.* 26(4):1055–64 (1994).

A "defense-related" gene refers to a plant nucleic acid whose expression increases when a plant is contacted with, or infected by, a pathogen. One of ordinary skill in the art will recognize that defense-related genes encode polypeptides with diverse predicted functions. Typically, defense-related genes encode polypeptides that may inhibit or destroy an invading pathogen or pathogen product. For instance, several defense-related genes are predicted to encode chitinases that can destroy the cell wall of invading fungal pathogens. The expression of many defense related genes is also induced or increased upon exposure to salicylic acid (SA) or SA analogs such as 2,6-dichloroisonicotinic acid (INA). Examples of defense-related genes include genes that encode pathogenesis-related proteins (PR) (see, e.g., Ward, et al. *Plant Cell* 3:1085–1094 (1991); Reuber et al. *Plant J.* 16(4):473–85 (1998); Heitz T, et al. *Mol Gen Genet* 245(2):246–54 (1994); and Stintzi et al. *Biochimie* 75(8):687–706 (1993)). Pathogenesis proteins include several proteins with homology to proteins with functions including β-1,3-glucanase and chitinases. Not all PR proteins have predicted functions (e.g., PR-1). Other examples of defense related genes include those encoding phytoalexins, phenylalanine ammonia lyase (PAL), proteinases, peroxidases, glutathoine-S transferases, lipoxygenases, as well as genes such as the rice Pir7b gene (see, e.g., Waspi, et al., *Eur. J. Biochem.* 254(1):32–7 (1998)), and SRG1 and SRG2 from alfalfa (see, e.g., Truesdell & Dickman, *Plant Mol Biol.* 33(4):737–43 (1997)), which were identified by the characteristic of induction upon pathogen infection. See, e.g., Hunt, et al. *Gene* 179(1):89–95 (1996); Fluhr, et al. *Biochem Soc Symp* 60:131–41 (1994); Bowles, et al. *Annu Rev Biochem* 59:873–907 (1990); Glazebrook, et al. *Annu Rev Genet* 31:547–69 (1997); Dixon, R., et al., Adv Genet. 28:165–234 (1990); Ward, E., et al., Plant Cell 3:1085–1094 (1991); Lawton, et al., Plant J. 10:71–82 (1996); and Friedrich, L., et al., Plant J. 10:61–70 (1996) for additional examples and reviews of defense-related genes.

"Pathogens" include, but are not limited to, viruses, bacteria, nematodes, fungi or insects (see, e.g., Agrios, *Plant Pathology* (Academic Press, San Diego, Calif.) 1988).

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., U.S.A.).

The phrase "substantially identical," in the context of two nucleic acids or polypeptides, refers to sequences or subsequences that have at least 60%, preferably 80%, most preferably 90–95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

One of skill in the art will recognize that two polypeptides can also be "substantially identical" if the two polypeptides are immunologically similar. Thus, overall protein structure may be similar while the primary structure of the two polypeptides display significant variation. Therefore a method to measure whether two polypeptides are substantially identical involves measuring the binding of monoclonal or polyclonal antibodies to each polypeptide. Two polypeptides are substantially identical if the antibodies specific for a first polypeptide bind to a second polypeptide with an affinity of at least one third of the affinity for the first polypeptide.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins &.Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, painvise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);

2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V); and

6) Phenylalanine (F), Tyrosine (Y), Tryptophan (W). (see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Low stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions.

In the present invention, genomic DNA or cDNA comprising ANT nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2× SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cased, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1× SSC at 45° C. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., an RNA gel or DNA gel blot hybridization analysis.

DESCRIPTION OF THE SPECIFIC EMBODIMENTS

The present invention provides the first definitive evidence that bZIP genes and their gene products interacts with, and are regulated by, NPR1, a key component in plant pathogen resistance. The present invention also provides for the first time rice and tomato bZIP polynucleotides encoding polypeptides that interact with NPR 1.

Because the bZIP gene product most likely functions as a transcription factor that binds to salicylic acid-responsive DNA elements (see, e.g. the postulated bZIP binding site in the PR-1 promoter: Lebel, E., et al., *Plant J.* 16, 223–234 (1998)), one of skill will recognize that desired phenotypes associated with altered bZIP activity can be obtained by modulating the expression or activity of bZIP-regulated genes. Any of the known methods described for increasing or decreasing expression or protein activity can be used for this invention.

Increasing BZIP Activity or BZIP Gene Expression

Any of a number of means well known in the art can be used to increase bZIP activity in plants. Enhanced expression is useful, for example, to enhance systemic resistance to pathogens. Any organ can be targeted, such as shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit. Alternatively, one or several bZIP genes can be expressed constitutively (e.g., using the CaMV 35S promoter).

Increased bZIP activity or bZIP expression can also be used to enhance resistance of plants to specific pathogens. Thus, for instance bZIP expression can be targeted to induce defense-related genes harmful to specific pathogens.

Increasing bZIP Gene Expression

Isolated sequences prepared as described herein can be used to introduce expression of a particular bZIP nucleic acid to increase gene expression using methods well known to those of skill in the art. Preparation of suitable constructs and means for introducing them into plants are described below.

One of skill will recognize that the polypeptides encoded by the genes of the invention, like other proteins, have different domains that perform different functions. Thus, the gene sequences need not be full length, so long as the desired functional domain of the protein is expressed. The distinguishing features of bZIP polypeptides, including the leucine zipper and basic domain, are discussed in Foley et al.

Plant J. 3:669–79 (1993) and Singh et al. Plant Cell 2:891–903 (1990). The bZIP polypeptides of the invention interact with NPR1.

Modified protein chains can also be readily designed utilizing various recombinant DNA techniques well known to those skilled in the art and described in detail below. For example, the chains can vary from the naturally occurring sequence at the primary structure level by amino acid substitutions, additions, deletions, and the like. These modifications can be used in a number of combinations to produce the final modified protein chain.

Modification of Eendogenous bZIP Genes

Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, X-rays or gamma rays can be used.

Alternatively, homologous recombination can be used to induce targeted gene modifications by specifically targeting the bZIP gene in vivo (see, generally, Grewal and Klar, Genetics 146: 1221–1238 (1997) and Xu et al., Genes Dev. 10: 2411–2422 (1996)). Homologous recombination has been demonstrated in plants (Puchta et al., Experientia 50: 277–284 (1994), Swoboda et al., EMBO J. 13: 484–489 (1994); Offringa et al., Proc. Natl. Acad. Sci. USA 90: 7346–7350 (1993); and Kempin et al. Nature 389:802–803 (1997)).

In applying homologous recombination technology to the genes of the invention, mutations in selected portions of an bZIP gene sequences (including 5' upstream, 3' downstream, and intragenic regions) such as those disclosed here are made in vitro and then introduced into the desired plant using standard techniques. Since the efficiency of homologous recombination is known to be dependent on the vectors used, use of dicistronic gene targeting vectors as described by Mountford et al., Proc. Natl. Acad. Sci. USA 91: 4303–4307 (1994); and Vaulont et al., Transgenic Res. 4: 247–255 (1995) are conveniently used to increase the efficiency of selecting for altered bZIP gene expression in transgenic plants. The mutated gene will interact with the target wild-type gene in such a way that homologous recombination and targeted replacement of the wild-type gene will occur in transgenic plant cells, resulting in suppression of bZIP activity.

Alternatively, oligonucleotides composed of a contiguous stretch of RNA and DNA residues in a duplex conformation with double hairpin caps on the ends can be used. The RNA/DNA sequence is designed to align with the sequence of the target bZIP gene and to contain the desired nucleotide change. Introduction of the chimeric oligonucleotide on an extrachromosomal T-DNA plasmid results in efficient and specific bZIP gene conversion directed by chimeric molecules in a small number of transformed plant cells. This method is described in Cole-Strauss et al., Science 273:1386–1389 (1996) and Yoon et al. Proc. Natl. Acad. Sci. USA 93: 2071–2076 (1996).

Other Means for Increasing bZIP Activity

One method to increase bZIP expression is to use "activation mutagenesis" (see, e.g. Hiyashi et al. Science 258:1350–1353 (1992)). In this method an endogenous bZIP gene can be modified to be expressed constitutively, ectopically, or excessively by insertion of T-DNA sequences that contain strong/constitutive promoters upstream of the endogenous bZIP gene. As explained below, preparation of transgenic plants overexpressing bZIP can also be used to increase bZIP expression. Activation mutagenesis of the endogenous bZIP gene will give the same effect as overexpression of the transgenic bZIP nucleic acid in transgenic plants. Alternatively, an endogenous gene encoding an enhancer of bZIP activity or expression of the endogenous bZIP gene can be modified to be expressed by insertion of T-DNA sequences in a similar manner and bZIP activity can be increased.

Another strategy to increase bZIP expression can be the use of dominant hyperactive mutants of bZIP by expressing modified bZIP transgenes. For example expression of modified bZIP with a defective domain that is important for interaction with a negative regulator of bZIP activity can be used to generate dominant hyperactive bZIP proteins. Alternatively, expression of truncated bZIP proteins which have only a domain that interacts with a negative regulator can titrate the negative regulator and thereby increase endogenous bZIP activity. Use of dominant mutants to hyperactivate target genes is described in Mizukami et al. Plant Cell 8:831–845 (1996).

Inhibition of bZIP Activity or Gene Expression

As explained above, bZIP activity is important in controlling the expression of a number of defense-related genes through interaction with the gene's promoters as well as with other proteins (e.g., RNA polymerase). Inhibition of bZIP gene expression activity can be used, for instance, to reduce pathogen resistance in plants. In particular, targeted expression of bZIP nucleic acids that inhibit endogenous gene expression (e.g., antisense or co-suppression) can be used to reduce pathogen resistance.

Inhibition of bZIP Gene Expression

The nucleic acid sequences disclosed here can be used to design nucleic acids useful in a number of methods to inhibit bZIP or related gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA translation (see, Bourque Plant Sci. (Limerick) 105: 125–149 (1995); Pantopoulos In Progress in Nucleic Acid Research and Molecular Biology, Vol. 48. Cohn, W. E. and K. Moldave (Ed.). Academic Press, Inc.: San Diego, Calif., U.S.A.; London, England, UK. p. 181–238; Heiser et al. Plant Sci. (Shannon) 127: 61–69 (1997)) and by preventing the accumulation of mRNA which encodes the protein of interest, (see, Baulcombe Plant Mol. Bio. 32:79–88 (1996); Prins and Goldbach Arch. Virol. 141: 2259–2276 (1996); Metzlaffet al. Cell 88: 845–854 (1997), Sheehy et al., Proc. Nat. Acad. Sci. USA, 85:8805–8809 (1988), and Hiatt et al., U.S. Pat. No. 4,801, 340).

The nucleic acid segment to be introduced generally will be substantially identical to at least a portion of the endogenous bZIP gene or genes to be repressed. The sequence, however, need not be perfectly identical to inhibit expression. The vectors of the present invention can be designed such that the inhibitory effect applies to other genes within a family of genes exhibiting identity or substantial identity to the target gene.

For antisense suppression, the introduced sequence also need not be full length relative to either the primary transcription product or fully processed mRNA. Generally, higher identity can be used to compensate for the use of a shorter sequence. Furthermore, the introduced sequence need not have the same intron or exon pattern, and identity of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 3500 nucleotides is especially preferred.

A number of gene regions can be targeted to suppress bZIP gene expression. The targets can include, for instance, the coding regions, introns, sequences from exon/intron junctions, 5' or 3' untranslated regions, and the like.

Another well-known method of suppression is sense co-suppression. Introduction of nucleic acid configured in the sense orientation has been recently shown to be an effective means by which to block the transcription of target genes. For an example of the use of this method to modulate expression of endogenous genes (see, Assaad et al. *Plant Mol. Bio.* 22: 1067–1085 (1993); Flavell *Proc. Natl. Acad. Sci. USA* 91: 3490–3496 (1994); Stam et al. *Annals Bot.* 79: 3–12 (1997); Napoli et al., *The Plant Cell* 2:279–289 (1990); and U.S. Pat. Nos. 5,034,323, 5,231,020, and 5,283,184).

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting identity or substantial identity.

For co-suppression, the introduced sequence, needing less than absolute identity, also need not be full length, relative to either the primary transcription product or fully processed mRNA. This may be preferred to avoid concurrent production of some plants that over-express the introduced sequence. A higher identity in a sequence shorter than full-length compensates for a longer, less identical sequence. Furthermore, the introduced sequence need not have the same intron or exon pattern, and identity of non-coding segments will be equally effective. Normally, a sequence of the size ranges noted above for antisense regulation is used. In addition, the same gene regions noted for antisense regulation can be targeted using co-suppression technologies.

Oligonucleotide-based triple-helix formation can also be used to disrupt bZIP gene expression. Triplex DNA can inhibit DNA transcription and replication, generate site-specific mutations, cleave DNA, and induce homologous recombination (see, e.g., Havre and Glazer *J. Virology* 67:7324–7331 (1993); Scanlon et al. *FASEB J.* 9:1288–1296 (1995); Giovannangeli et al. *Biochemistry* 35:10539–10548 (1996); Chan and Glazer *J. Mol. Medicine* (Berlin) 75: 267–282 (1997)). Triple helix DNAs can be used to target the same sequences identified for antisense regulation.

Catalytic RNA molecules or ribozymes can also be used to inhibit expression of bZIP genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. Thus, ribozymes can be used to target the same sequences identified for antisense regulation.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Zhao and Pick, *Nature* 365:448–451 (1993); Eastham and Ahlering, *J. Urology* 156:1186–1188 (1996); Sokol and Murray, *Transgenic Res.* 5:363–371 (1996); Sun et al., *Mol. Biotechnology* 7:241–251 (1997); and Haseloff et al., *Nature,* 334:585–591 (1988).

Modification of Endogenous BZIP Genes

Methods for introducing genetic mutations described above can also be used to select for plants with decreased bZIP expression.

Other means for Inhibiting bZIP Activity

BZIP activity may be modulated by eliminating the proteins that are required for bZIP cell-specific gene expression. Thus, expression of regulatory proteins and/or the sequences that control bZIP gene expression can be modulated using the methods described here.

Another strategy is to inhibit the ability of a bZIP protein to interact with itself or with other proteins. This can be achieved, for instance, using antibodies specific to bZIP. In this method cell-specific expression of bZIP-specific antibodies is used to inactivate functional domains through antibody:antigen recognition (see, Hupp et al., *Cell* 83:237–245 (1995)). Interference of activity of a bZIP interacting protein(s) can be applied in a similar fashion. Alternatively, dominant negative mutants of bZIP can be prepared by expressing a transgene that encodes a truncated bZIP protein. Use of dominant negative mutants to inactivate target genes in transgenic plants is described in Mizukami et al., *Plant Cell* 8:831–845 (1996).

Purification of bZIP Polypeptides

Either naturally occurring or recombinant bZIP polypeptides can be purified for use in functional assays. Naturally occurring bZIP polypeptides can be purified, e.g., from plant tissue and any other source of a bZIP homolog. Recombinant bZIP polypep ides can be purified from any suitable expression system.

The bZIP polypeptides may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,64; Ausubel et al., supra, and Sambrook et al., supra).

A number of procedures can be employed when recombinant bZIP polypeptides are being purified. For example, proteins having established molecular adhesion properties can be reversible fused to the bZIP polypeptides. With the appropriate ligand, the bZIP polypeptides can be selectively adsorbed to a purification column and then freed from the column in a relatively pure form. The fused protein is then removed by enzymatic activity. Finally the bZIP polypeptides could be purified using immunoaffinity columns.

Isolation of bZIP Nucleic Acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning-A Laboratory Manual*, Cold Spring Harbor Laboratory, Cold Spring Harbor, New York, (1989) or Current Protocols in Molecular Biology Volumes 1–3, John Wiley & Sons, Inc. (1994–1998).

The isolation of bZIP nucleic acids may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as leaves, and a cDNA library which contains a bZIP gene transcript is prepared from the mRNA. Alternatively, cDNA may be prepared from mRNA extracted from other tissues in which bZIP genes or homologs are expressed.

The cDNA or genomic library can then be screened using a probe based upon the sequence of a cloned bZIP gene disclosed here. Probes may be used to hybridize with genomic DNA or cDNA sequences to isolate homologous genes in the same or different plant species. Alternatively, antibodies raised against a bZIP polypeptide can be used to screen an mRNA expression library.

Alternatively, the nucleic acids of interest can be amplified from nucleic acid samples using amplification techniques. For instance, polymerase chain reaction (PCR) technology can be used to amplify the sequences of bZIP genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see *PCR Protocols: A Guide to Methods and Applications*. (Innis, M, Gelfand, D., Sninsky, J. and White, T., eds.), Academic Press, San Diego (1990). Appropriate primers and probes for identifying bZIP sequences from plant tissues are generated from comparisons of the sequences provided here (e.g. SEQ ID NO: 1, SEQ ID NO:3, etc.).

Polynucleotides may also be synthesized by well-known techniques as described in the technical literature. See, e.g., Carruthers et al., *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill. Such genes include for example, ACT11 from Arabidopsis (Huang et al. *Plant Mol. Biol.* 33:125–139 (1996)), Cat3 from Arabidopsis (GenBank No. U43147, Zhong et al., *Mol. Gen. Genet.* 251:196–203 (1996)), the gene encoding stearoyl-acyl carrier protein desaturase from *Brassica napus* (Genbank No. X74782, Solocombe et al. *Plant Physiol.* 104:1167–1176 (1994)), GPc1 from maize (GenBank No. X15596, Martinez et al. *J. Mol. Biol* 208:551–565 (1989)), and Gpc2 from maize (GenBank No. U45855, Manjunath et al., *Plant Mol. Biol.* 33:97–112 (1997)).

Alternatively, the plant promoter may direct expression of bZIP nucleic acid in a specific tissue, organ or cell type (i.e. tissue-specific promoters) or may be otherwise under more precise environmental or developmental control (i.e. inducible promoters). Examples of environmental conditions that may effect transcription by inducible promoters include anaerobic conditions, elevated temperature, the presence of light, or sprayed with chemicals/hormones. Tissue-specific promoters can be inducible. Similarly, tissue-specific promoters may only promote transcription within a certain time frame of developmental stage within that tissue. Other tissue specific promoters may be active throughout the life cycle of a particular tissue. One of skill will recognize that a tissue-specific promoter may drive expression of operably linked sequences in tissues other than the target tissue. Thus, as used herein a tissue-specific promoter is one that drives expression preferentially in the target tissue or cell type, but may also lead to some expression in other tissues as well.

A number of tissue-specific promoters can also be used in the invention. For instance, promoters that direct expression of nucleic acids in leaves, roots or flowers are useful for enhancing resistance to pathogens that infect those organs. For expression of a bZIP polynucleotide in the aerial vegetative organs of a plant, photosynthetic organ-specific promoters, such as the RBCS promoter (Khoudi, et al., *Gene* 197:343, 1997), can be used. Root-specific expression of bZIP polynucleotides can be achieved under the control of the root-specific ANR1 promoter (Zhang & Forde, *Science*, 279:407, 1998). Any strong, constitutive promoters, such as the CaMV 35S promoter, can be used for the expression of bZIP polynucleotides throughout the plant.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *Embo. J* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496–498 (1984), and Fraley et al. *Proc. Natl. Acad. Sci. USA* 80:4803 (1983) and *Gene Transfer to Plants*, Potrykus, ed. (Springer-Verlag, Berlin 1995).

Transformed plant cells which are derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The nucleic acids of the invention can be used to confer desired traits on essentially any plant. Thus, the invention has use over a broad range of plants, including species from the genera Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna, and Zea.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Using known procedures one of skill can screen for plants of the invention by detecting the increase or decrease of bZIP mRNA or protein in transgenic plants. Means for detecting and quantitating mRNAs or proteins are well known in the art.

Methods of Enhancing Plant Resistance to Pathogens

The present invention provides for method of enhancing plant resistance to pathogens by modulating the expression and/or activity of bZIP polynucleotides and/or polypeptides. Without limiting the invention to a particular mechanism of operation, increased expression of bZIP polynucleotides or bZIP polypeptides can be used to enhance resistance of plants to pathogens. Resistance can be enhanced, for instance, relative to a pathogen species or genus or systemic acquired resistance can be induced by increased expression of bZIP polynucleotides or bZIP polypeptides. Alternatively, or in combination, bZIP polynucleotides or bZIP polypeptides can be modified to enhance resistance, e.g., by increasing or decreasing bZIP polypeptides' interactions with other components important in plant pathogen resistance.

Without limiting the invention to a particular mechanism of operation, one possible mechanism by which bZIP polypeptides modulate resistance, for example, is by interacting with the promoters of defense-related genes. Interaction of bZIP polypeptides with these promoters may lead directly to increased transcription of defense-related transcripts, thereby enhancing resistance to pathogens. Alternatively, bZIP polypeptides may interact with promoters of other genes as well as with other regulatory factors, thereby modulating expression of defense related genes or other genes involved in resistance. For instance, bZIP polypeptides may interact with a transcriptional repressor, thereby allowing for the expression of defense-related genes.

Selecting for Plants With Enhanced Resistance

Plants with enhanced resistance can be selected in many ways. One of ordinary skill in the art will recognize that the following methods are but a few of the possibilities. One method of selecting plants with enhanced resistance is to determine resistance of a plant to a specific plant pathogen. Possible pathogens include, but are not limited to, viruses, bacteria, nematodes, fungi or insects (see, e.g., Agrios, *Plant Pathology* (Academic Press, San Diego, Calif.) (1988)). One of skill in the art will recognize that resistance responses of plants vary depending on many factors, including what pathogen or plant is used. Generally, enhanced resistance is measured by the reduction or elimination of disease symptoms when compared to a control plant. In some cases, however, enhanced resistance can also be measured by the production of the hypersensitive response (HR) of the plant (see, e.g., Staskawicz et al. *Science* 268(5211): 661–7 (1995)). Plants with enhanced resistance can produce an enhanced hypersensitive response relative to control plants.

Enhanced resistance can also be determined by measuring the increased expression of a gene operably linked a deferise related promoter. Measurement of such expression can be measured by quantitating the accumulation of RNA or subsequent protein product (e.g., using northern or western blot techniques, respectively (see, e.g. Sambrook et al. and Ausubel et al.). A possible alternate strategy for measuring defense gene promoter expression involves operably linking a reporter gene to the promoter. Reporter gene constructs allow for ease of measurement of expression from the promoter of interest. Examples of reporter genes include: β-gal, GUS (sec, e.g., Jefferson, R. A., et al., *EMBO J* 6: 3901–3907 (1987), green fluorescent protein, luciferase, and others.

The following Examples are offered by way of illustration, not limitation.

EXAMPLE 1

This example shows that Nifl, a tomato bZIP polypeptide, interacts with a tomato NPR1 ortholog in a yeast two-hybrid system.

MATERIALS AND METHODS

Strains and Plasmids

The yeast two-hybrid system that contains the yeast strain, EGY48, and plasmids pEG202, pSH18-34, pJK101, pRFHM1, pSH17-4, and pJG4-5 was obtained from R. Brent (Gyuris, J., et al. *Cell* 75:791–803 (1993)). The full-length tomato NPR1 homolog was cloned into pEG202 after amplification from the CDNA clone (pTomNPR1) using PCR. The full-length *A. thaliana* NPR1 cDNA was amplified from pKExNPR1 (Cao, H., et al. *Cell* 88:57–63 (1997)) and cloned into pEG202 similarly. PCR was also used to construct the truncated NPR1 baits. $pEGNPR1_{1-177}$ encodes the amino terminal 177 amino acids of NPR1, $pEGNPR1_{1-432}$ contains the amino terminal portion and the ankyrin repeats, and $pEGNPR1_{178-593}$ encodes the ankyrin repeats and the carboxyl end of NPR1. The *A. thaliana* bZIP transcription factor genes AHBP-1b, TGA6, and OBF5 were obtained by PCR from a cDNA preparation and cloned into pJG4-5. AHBP-1b and OBF5 were also cloned into pET24C (+) (Novagen) to add a $(His)_6$-tag (SEQ ID NO:18) at the carboxyl end of the protein. The resulting plasmids were designated pET-AHBP-1b and pET-OBF5. The bait constructs containing the npr1-1 and npr1-2 mutations (Cao, H., et al. *Cell* 88:57–63 (1997)) were generated by site-directed mutagenesis using a PCR-based "link scanning" method (Li, X. & Shapiro, L. *Nucleic Acids Res.* 21:3745–3748 (1993)).

Isolation of an NPR1 Homolog From Tomato

Approximately one million plaques of a tomato leaf cDNA library (Martin, G. B., et al. *Science* 262:1432–1436 (1993)) were screened using both an *A. thaliana* NPR1 cDNA and an NPR1 homolog from *Nicotiana glutinosa* (M. Kinkema and X. Dong, unpublished data). Colony/Plaque screen nylon filters (NEN Life Science Products) were hybridized at 37° C. in 40% formamide, 5×SSC, 5×Denhardts, 1% SDS, and 10% dextran sulfate. The final wash was for 20 minutes at 37° C. in 2×SSC and 1% SDS. Three independent clones were sequenced and found to be identical in their overlapping regions. The clone that contains the full-length cDNA was designated pTomNPR1.

Yeast Two-Hybrid Screen and Assay

The yeast two-hybrid screen was performed as described (Finley, R. L. et al. (1996) in *DNA Cloning-Expression Systems: A Practical Approach*, eds. Glover D. & Hames B. D (Oxford University Press, Oxford, England), pp. 169–203). The prey library was constructed in plasmid pJG4-5 using cDNA (average size of 1.8 kb) extracted from TMV-infected tomato VF36 leaves and contains $10^7$ independent clones.

Results

Tomato NPR1 Homolog Interacts With a bZIP Transcription Factor in the Yeast Two-Hybrid Screen To identify genes that encode NPR1-interactors, we performed a yeast two-hybrid screen using a full-length tomato NPR1 homolog as the bait (pEGTomNPR1) and a cDNA library made from RNA extracted from TMV-infected tomato leaf tissue (kindly provided by Dr. B. Baker, USDA). The tomato NPR1 cDNA clone used in our yeast two-hybrid screen is a true homolog of the A. thaliana NPR1 because significant homology (54% identity and 73% similarity) is detected throughout the protein and the functionally important residues as defined by various nprl mutant alleles are conserved in this clone.

The cDNA library and the bait plasmid pEGTomNPR1 were co-transfomed into yeast strain EYG48 and $2.5 \times 10^6$ colonies were obtained. From these primary transformants, $2.5 \times 10^7$ cells were plated onto leucine drop-out plates. Seven distinct classes of tomato genes were found to interact with TomNPR1 in the yeast two-hybrid system. One class, NIF1 (NPR-1-Interacting Factor 1) was characterized in more detail. The NIF1 plasmid (pJGNIF1) was isolated and re-transforrned into EYG48 to confirm the interaction. Colonies carrying both pJGNIF1 and pEGTomNPR1 grew on plates lacking leucine, and turned dark blue on X-gal plates within 24 hours. The restoration of leucine prototrophy and the expression of β-galactosidase activity were dependent on the presence of galactose, indicating that the expression of NIF1 driven by the promoter of the yeast GAL1 gene was required for the expression of both reporter genes. This clone was also transformed into EGY48 together with vector pEG202 to test whether NIF1 by itself activates the transcription of the reporter genes. Expression of NIF1 alone did not restore leucine prototrophy or result in detectable β-galactosidase activity.

EXAMPLE 2

This example shows that AHBP-1b and TGA6, two Arabidopsis bZIP polypeptides related to Nifl, bind to Arabidopsis NPR1 in the yeast two-hybrid system. *Arabidopsis thaliana* NPR1 Interacts Strongly with AHBP-1b and TGA6 but Weakly with OBF5 in the Yeast Two-Hybrid System.

NIF1 was sequenced and a search of the GenBank Database identified three independent, closely related *A. thaliana* genes encoding the bZIP transcription factors AHBP-1b (Kawata, et al. *Nucleic Acids Res.* 20:1141 (1992)), TAG6 (Xiang, et al. *Plant Mol. Biol.* 34:403–415 (1997)), and OBF5 (Zhang, et aL *Plant J.* 4:711–716 (1993)). Sequence comparisons of NIF1, AHBP-1b, TAG6, and OBF5 reveal that the NIF1 clone identified in the yeast two-hybrid screen encodes the carboxyl two thirds of a bZIP transcription factor, which does not include the DNA binding or leucine zipper domains. The NIF1 clone shares 69–75% identity and 83–87% similarity with these A. *thaliana* homologs at the amino acid level.

To determine whether *A. thaliana* NPR1 interacts with the A. *thaliana* homologs of NIF1, DNA fragments containing the full-length AHBP-1b, TGA6 and OBF5 genes were amplified and cloned into pJG4-5. Interactions between the A. *thaliana* NPR1 and all three transcription factors were then tested in the yeast two-hybrid system. As observed for TomNPR1 and NIF1, where 1286 units of β-galactosidase activity were detected, A. *thaliana* NPR1 interacts strongly with AHBP-1b and TGA6, resulting in 673 and 372 units of β-galactosidase activity, respectively. Intriguingly, the interaction between NPR1 and OBF5 is much weaker with only 7.6 units of β-galactosidase activity.

EXAMPLE 3

This example shows that AHBP-1b and OBF5 interact with Arabidopsis NPR1 protein and that AHBP-1b interacts with the NPR1 domain containing ankyrin repeats.

Materials and Methods

Over-Expression and Purification of the Transcription Factor Proteins

The *E. coli* strain BL21(DE3) caitying pET-AHBP-1b or pET-OBF5 was grown ($OD_{600}$=1.0) in LB medium (1 liter) and the expression of AHBP-1b or OBF5 was induced by addition of IPTG (0.1 mM). After two hours, the bacteria were harvested, ground in alumina powder (2 times the weight of the cell pellet), and then resuspended in 50 ml of buffer (O mM Tris-HCl, pH 7.5, 50 mM KCl, 1×proteinase inhibitor cocktail (21), 6 mM 2-mercaptoethanol, and 10% glycerol). The cell extract was spun twice and Ni-NTA resin (Qiagen) was added to the supernatant and incubated for 1 hour. The mix was loaded into a column and washed with a washing buffer (1M KCl, 50 mM Tris-HCl, pH 7.5, 10% glycerol, 6 mM 2-mercaptoethanol, and 10 mM imidazole). The proteins were then eluted in a buffer (50 mM Tris-HCl, pH 7.5, 50 mM KCl, 150 mM imidazole, 6 mM 2-mercaptoethanol, and 10% glycerol). The eluted protein solution was dialyzed against 10 mM Tris-HCl, pH 7.5, 50 mM KCl , 6 mM 2-mercaptoethanol, and 10 % glycerol.

Over-Expression of NPR1 Using the Baculovirus System

The NPR1 cDNA was first cloned into pVL1392 by PCR using the restriction sites NotI and BglII, and then recombined in vivo into BaculoGold (PharMingen). The amplified virus preparation was used to infect Sf9 insect cells ($2 \times 10^6$ cells/ml). The cells were harvested and the total protein extract was prepared as described (PharMingen). The presence of NPR1 in the protein extract was confirmed using an antiserum prepared against the carboxyl terminal 16 amino acids of the protein (Cao, et al., *Proc. Nati. Acad. Sci. USA* 95:6531–6536 (1998)).

In vitro Analysis of Protein-Protein Interactions

Partially purified, His-tagged transcription factors (10 µg) were mixed in a binding buffer (50 mM Tris-HCl, pH 7.5, 50 mM KCl, 1×proteinase inhibitor cocktail, 6 mM 2-mercaptoethanol, and 10% glycerol) with the insect cell extract (50 µl) expressing *A. thaliana* NPR1. The protein mix was incubated on ice for 2 hours. Ni-NTA resin was then added to the protein mix and incubated for another hour. The Ni-NTA resin was pelleted and washed five times with a washing buffer (50 mM KCl, 50 mM Tris-HCl, pH 7.5 , 10% glycerol, 6 mM 2-mercaptoethanol, and 10 mM imidazole). Proteins were eluted from the Ni-NTA in a buffer (50 mM Tris-HCl, pH 7.5, 50 mM KCl, 150 mM imidazole, 6 mM 2-mercaptoethanol, and 10% glycerol), and a quarter of the proteins were run on an SDS-PAGE gel and subsequently transferred to a Protran nitrocellulose membrane (Schleicher & Schuell). Immunoblot analysis was performed using antibodies raised against NPR1 (see, Cao, et al.) to check for co-purification of NPR1 with the His-tagged transcription factors.

Results

NPR1 Interacts With AHBP-1B and OBF5 In Vitro

To test whether NPR1 interacts with AHBP-1b and OBF5 in vitro, His-tagged AHBP-1b and OBF5 proteins were expressed in *E. coli* and purified using a Ni-NTA column. Purified AHBP-1b or OBF5 protein was then mixed with extracts containing baculovirus-expressed NPR1 protein. The AHBP-1b and OBF5 proteins were then "pulled down" using Ni-NTA resin. Immunoblot analysis using an antiserum against NPR1 showed that the NPRl protein co-purified with AHBP-1b, demonstrating that AHBP-1b physically associates with NPR1 in vitro. As a negative control, Ni-NTA resin alone was mixed with the NPR1 protein extract. The results showed that NPR1 does not bind to Ni-NTA resin by itself. When the partially purified OBF5 protein preparation was used in the experiments, co-purification of NPR1 was also detected. This indicates that OBF5 can interact with NPR1 in vitro; the assay was not sensitive enough to detect the difference in binding affinities of NPR1 to AHBP-1b and to OBF5 as seen in the yeast two-hybrid screen.

NPR1 Interacts With AHBP-1b through the Ankyrin-repeat Domain

To define the region in NPR1 that directly interacts with AHBP-1b, NPR1 gene fragments encoding different domains of the protein were cloned into the bait vector. The truncations were made at the exon-intron boundaries because these boundaries are conserved between NPR1 and its homologs and therefore, may define distinct functional domains of the protein. $pEGNPR1_{1-177}$ carries the first exon of the NPR1 gene and encodes the amino terminal 177 residues; $pEGNPR1_{1-432}$ includes both the amino terminal and the ankyrin-repeat domain of NPR1 (exons 1 and 2); $pEGNPR1_{178-593}$ contains the ankyrin-repeat domain and the carboxyl end of NPR1 (exons 2, 3, and 4). These truncated NPR1 proteins were co-expressed with the transcription factor AHBP-1b in yeast and β-galactosidase reporter gene activity was measured. In yeast expressing $NPR1_{11-432}$ and AHBP-1b, the β-galactosidase reporter gene activity (522 units) was similar to that observed in the cells expressing the full-length NPR1 (673 units). This shows that NPR1 interacts with AHBP-1b through the amino terminal and/or the ankyrin-repeat domain. However, in cells expressing $NPR1_{178-593}$, which lacks the amino terminal 177 residues, the NPR1-AHBP- lb interaction still occurred, even though at a lower level (17.6 units). This implies that the ankyrin-repeat domain of NPR1 directly interacts with AHBP-1b. Because $NPR1_{178-593}$ interacts with AHBP-1b with a lower affinity than the full-length NPR1, the amino terminal region of NPR1 may also contribute to the NPR1 -AHBP-1b interaction. Because the amino terminal region alone does not interact with AHBP-1b, this region probably serves to stabilize the ankyrin-repeat domain. Surprisingly, the amino terminal region of NPR1 alone seems to have a low level of intrinsic transactivation activity (6 units) detected when it is expressed in yeast without the prey.

EXAMPLE 4

This example shows that NPR1 mutants do not interact with AHBP-1b and TGA6.

The NPR1 -AHBP-1b and NPR1 -TGA6 Interactions are Abolished by the npr1 Mutations To further determine the specificity of the NPR1 -AHBP-1b and NPR1-TGA6 interactions, we generated bait constructs containing either the npr1-2 or npr1-2 point mutations (Cao, et al. *Cell* 88:57–63 (1997)). In npr1-1, the highly conserved $histidine_{334}$ in the ankyrin-repeat domain is changed to a tyrosine while in npr1-2, $cysteinel_{150}$ in the amino terminal region of NPR1 is converted to a tyrosine. These mutant constructs were co-transformed into yeast with either AHBP-1b or TGA6 clone and β-galactosidase activity was measured in the resulting transformants. In both transfornants, only background levels of β-galactosidase activity were detected indicating that the npr1-2 and npr1-1 mutations abolish the ability of NPR1 to interact with AHBP-1b or TGA6. Western blot analysis of the total protein preparations from these yeast strains showed that npr1-1 and npr1-2 were expressed at levels similar to the wild-type NPR1 protein. Therefore, the lack of reporter gene expression was not a result of poor expression of the mutant bait proteins, but a consequence of impaired interaction caused by the point mutations.

EXAMPLE 5

This example shows that AHBP-1b binds to the PR-1 promoter.

Methods and Materials
Gel Mobility Shift Assay

Oligonucleotide probes used in the gel mobility shift assay were designed according to the sequence of the INA- and SA-responsive promoter element identified in the *A. thaliana* PR-1 gene (Lebel, et al. *Plant J.* 16:223–234 (1998)). The wild-type oligonucleotide probe used in the assay was 5'CTCTACGTCACTATTTTACTTACGTCATAGATG3' (SEQ ID NO:19) while the mutant used was 5'CTCTAttctACTATTTTACTTAttctATAGATG3'(SEQ ID NO: 20). Each strand of the probes was end-labeled by incubating 10 pmol of oligonucleotide in a 20 µl reaction with 10 units of polynucleotide kinase (NEB) and 50 µCi of [γ-$^{32}$P] ATP. The two complementary strands were then mixed, annealed, and purified using a Nucleotide Removal Kit (Qiagen). For each binding reaction, 1 µg of the partially purified transcription factor protein was added together with 100 ng of poly [dI-dC] and 20 µl of binding buffer (12 mM HEPES, pH7.9, 60 mM KCl, 2 mM MgCl$_2$, 10% glycerol, 1 mM DTT, 1×protease inhibitor cocktail). The mixture was incubated at room temperature for 10 min before addition of the labeled probe (30,000 cpm/reaction). The reaction was incubated for another 30 min and then run on a 4% (w/v) native polyacrylamide gel in 0.5×TBE buffer. After electrophoresis, the gel was dried and autoradiographed.

Results
AHBP-1b Binds to a Promoter Element in the PR-1 Gene

To analyze the role of AHBP-1b in regulating SA-responsive gene expression, a gel mobility shift assay was performed to determine if AHBP-1b could bind to a promoter fragment of the PR-1 gene. The *A. thaliana* PR-1 gene promoter fragment used contains an as-1-like element, which has been identified previously as a binding motif of bZIP transcription factors and has been shown by linker scanning mutagenesis to be essential for both INA- and SA-induced PR-1 gene expression in planta (Lebel, E., et al. *Plant J.* 16:223–234 (1998)). With the partially purified transcription factor (1 µg), a mobility shift was observed for the oligonucleotide probe. To demonstrate that this mobility shift was due to the binding of AHBP-1b and not other nonspecific proteins in the preparation, a control reaction was carried out using an unrelated protein purified under identical conditions. The control protein preparation did not bind to the probe. To further examine the specificity of the binding, a competition experiment was performed using an excess amount of unlabeled probe containing the bZIP transcription factor binding site. When a 40-fold excess of unlabeled oligonucleotides were included in the reaction, binding of AHBP-1b to the labeled probe was completely abolished. As a negative control, an oligonucleotide containing point mutations in the bZIP binding motif was also used in the competition experiment. Binding of AHBP-1b to the labeled probe was unaffected by the presence of the mutant fragment even when its concentration was 100 times higher than the labeled probe.

EXAMPLE 6

This example shows four rice bZIP gene products, MN1, MN8, MN38 and MN140, bind to Arabidopsis NPR1 in the yeast two-hybrid system.

Results
Four Rice bZIP Polypeptides Interact With NPR1 in the Yeast Two-Hybrid System A rice cDNA library (unpublished; Song, W. and Ronald, P.) prepared in the pAD-GAL4 vector was screened using a full-length Arabidopsis Npr1 cDNA as the bait. The Arabidopsis NPR1 bait was cloned into the SmaI and BglII sites of plasmid pMC86, which was constructed by replacing the GAL4 activation domain in pPC86 with the GAL4 DNA binding domain (GAL4DB) in pPC97. NPR1 was expressed as a GAL4DB::NPR1 fusion protein in the yeast host HF7c (Clontech, Palo Alto, Calif.). After screening approximately 20 million yeast transformants, four independent clones were isolated that displayed histidine prototrophy and were lacZ positive. These clones are hereafter called MN1, MN8, MN38, and MN140.

The 5' ends of MN1 and MN8 cDNAs were obtained by running nested PCR reactions for each clones using the same rice library cDNA as the template. The primary reaction was carried out with anchor primer SS20 (5'AGGGATGTTTAATACCACTAC; SEQ ID NO:21) and gene-specific primer mn1-1 (5'GAAGCCATGACTGCACCA; SEQ ID NO:22) for MN1 or primer mn8-1 (5'TTATCGTCGGTATCCAGGA; SEQ ID NO:23) for MN8. The secondary reaction used anchor primer (5'ACCCGGGAGAGATCGAATTCGGCACGA; SEQ ID NO:24) and gene-specific primer mn1-2 (5'CACCACTATGTCCGTTTTC; SEQ ID NO:25) for MN1 or primer mn8-2 (5' GGACTGTTGA5GGTCAGT; SEQ ID NO:26) for MN8. PCR products were cloned in the pCR-BluntII-TOPO (Invitrogen, Carlsbad, Calif.) plasmid vector. Two clones for each were sequenced. The MN8 clone obtained from two-hybrid screens appeared to contain the complete cDNA coding region when the sequences were compared. The MN1 sequence encoding the first 18 amino acids is combined with that of the original MN1 clone to give a complete cDNA coding sequence.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. An isolated nucleic acid construct comprising a bZIP polynucleotide sequence that:
   a) is at least 95% identical over at least 500 base pairs to SEQ ID NO:1, SEQ ID NO:3, SEQ ID NO:5, SEQ ID NO:7 or SEQ ID NO:9, or
   b) encodes a polypeptide comprising SEQ ID NO:2, SEQ ID NO:4, SEQ ID NO:6, SEQ ID NO:8 or SEQ ID NO:10.

2. The construct of claim 1, wherein the bZIP polynucleotide sequence is derived from tomato.

3. The construct of claim 1, wherein the bZIP polynucleotide sequence is derived from rice.

4. The construct of claim 1, wherein the bZIP polynucleotide sequence is SEQ ID NO:1.

5. The construct of claim 1, wherein the bZIP polynucleotide sequence is SEQ ID NO:3.

6. The construct of claim 1, wherein the bZIP polynucleotide sequence is SEQ ID NO:5.

7. The construct of claim 1, wherein the bZIP polynucleotide sequence is SEQ ID NO:7.

8. The construct of claim 1, wherein the bZIP polynucleotide sequence is SEQ ID NO:9.

9. The construct of claim 1, wherein the bZIP polynucleotide sequence encodes SEQ ID NO:2.

10. The construct of claim 1, wherein the bZIP polynucleotide sequence encodes SEQ ID NO:4.

11. The construct of claim 1, wherein the bZIP polynucleotide sequence encodes SEQ ID NO:6.

12. The construct of claim 1, wherein the bZIP polynucleotide sequence encodes SEQ ID NO:8.

13. The construct of claim 1, wherein the bZIP polynucleotide sequence encodes SEQ ID NO:10.

14. The construct of claim 1, further comprising a promoter operably linked to the bZIP polynucleotide sequence.

15. The construct of claim 14, wherein the promoter is a tissue-specific promoter.

16. The construct of claim 14, wherein the promoter is a constitutive promoter.

17. A transgenic plant comprising a recombinant expression cassette comprising a plant promoter operably linked to a bZIP polynucleotide sequence that encodes a polypeptide capable of interacting with NPR1, wherein the polynucleotide:
   a) is at least 95% identical over at least 500 base pairs to SEQ ID NO:1, SEQ ID NO:3, SEQ ID NO:5, SEQ ID NO:7 or SEQ ID NO:9, or
   b) encodes a polypeptide comprising SEQ ID NO:2, SEQ ID NO:4, SEQ ID NO:6, SEQ ID NO:8 or SEQ ID NO:10.

18. The transgenic plant of claim 17, wherein the bZIP polynucleotide sequence is SEQ ID NO:1.

19. The transgenic plant of claim 17, wherein the bZIP polynucleotide sequence is SEQ ID NO:3.

20. The transgenic plant of claim 17, wherein the bZIP polynucleotide sequence is SEQ ID NO:5.

21. The transgenic plant of claim 17, wherein the bZIP polynucleotide sequence is SEQ ID NO:7.

22. The transgenic plant of claim 17, wherein the bZIP polynucleotide sequence is SEQ ID NO:9.

23. The transgenic plant of claim 17, wherein the plant promoter is a heterologous promoter.

24. The transgenic plant of claim 17, wherein the plant is rice.

25. The transgenic plant of claim 17, wherein the plant is tomato.

26. The transgenic plant of claim 17, wherein the bZIP polynucleotide sequence encodes a polypeptide comprising SEQ ID NO:2.

27. The transgenic plant of claim 17, wherein the bZIP polynucleotide sequence encodes a polypeptide comprising SEQ ID NO:4.

28. The transgenic plant of claim 17, wherein the bZIP polynucleotide sequence encodes a polypeptide comprising SEQ ID NO:6.

29. The transgenic plant of claim 17, wherein the bZIP polynucleotide sequence encodes a polypeptide comprising SEQ ID NO:8.

30. The transgenic plant of claim 17, wherein the bZIP polynucleotide sequence encodes a polypeptide comprising SEQ ID NO:10.

31. A method of enhancing resistance to pathogens in a plant, the method comprising
   a) introducing into the plant a recombinant expression cassette comprising a plant promoter operably linked to the bZIP polynucleotide sequence of claim 1, and
   b) selecting a plant with enhanced resistance.

32. The method of claim 31, wherein the selecting step is performed by measuring for increased expression from the promoter of a defense-related gene.

33. The method of claim 31, wherein the plant is rice.

34. The method of claim 31, wherein the plant is tomato.

35. The method of claim 31, wherein the bZIP polynucleotide sequence encodes a bZIP polypeptide comprising SEQ ID NO:2.

36. The method of claim 31, wherein the bZIP polynucleotide sequence encodes a bZIP polypeptide comprising SEQ ID NO:4.

37. The method of claim 31, wherein the bZIP polynucleotide sequence encodes a bZIP polypeptide comprising SEQ ID NO:6.

38. The method of claim 31, wherein the bZIP polynucleotide sequence encodes a bZIP polypeptide comprising SEQ ID NO:8.

39. The method of claim 31, wherein the bZIP polynucleotide sequence encodes a bZIP polypeptide comprising SEQ ID NO:10.

40. The method of claim 31, wherein the bZIP polynucleotide sequence comprising SEQ ID NO:1.

41. The method of claim 31, wherein the bZIP polynucleotide sequence comprising SEQ ID NO:3.

42. The method of claim 31, wherein the bZIP polynucleotide sequence comprising SEQ ID NO:5.

43. The method of claim 31, wherein the bZIP polynucleotide sequence comprising SEQ ID NO:7.

44. The method of claim 31, wherein the bZIP polynucleotide sequence comprising SEQ ID NO:9.

45. The method of claim 31, wherein the promoter is a tissue-specific promoter.

46. The method of claim 31, wherein the promoter is a constitutive promoter.

* * * * *